US011457946B1

(12) United States Patent
Robinson et al.

(10) Patent No.: US 11,457,946 B1
(45) Date of Patent: Oct. 4, 2022

(54) ATHERECTOMY DEVICES AND METHODS

(71) Applicant: Cardio Flow, Inc., St. Paul, MN (US)

(72) Inventors: Paul Joseph Robinson, Mahtomedi, MN (US); Cassandra Ann Piippo Svendsen, Blaine, MN (US); Albert Selden Benjamin, St. Paul, MN (US); Charles Anthony Plowe, Blaine, MN (US)

(73) Assignee: Cardio Flow, Inc., St. Paul, MN (US)

( * ) Notice: Subject to any disclaimer, the term of this patent is extended or adjusted under 35 U.S.C. 154(b) by 436 days.

(21) Appl. No.: 16/672,900

(22) Filed: Nov. 4, 2019

Related U.S. Application Data

(63) Continuation of application No. 16/146,809, filed on Sep. 28, 2018, now Pat. No. 10,463,390, which is a continuation of application No. 15/988,160, filed on May 24, 2018, now abandoned.

(51) Int. Cl.
*A61B 17/3207* (2006.01)
*A61B 17/32* (2006.01)

(52) U.S. Cl.
CPC ........... *A61B 17/320758* (2013.01); *A61B 17/320725* (2013.01); *A61B 2017/320004* (2013.01); *A61B 2017/320733* (2013.01); *A61B 2017/320741* (2013.01); *A61B 2017/320766* (2013.01)

(58) Field of Classification Search
CPC .... A61B 2017/320766; A61B 17/3207; A61B 17/320725; A61B 2017/320733; A61B 17/320758; A61B 2017/320004; A61B 17/32002
See application file for complete search history.

(56) References Cited

U.S. PATENT DOCUMENTS

| | | | |
|---|---|---|---|
| 1,431,416 | A | 10/1922 | Parsons |
| 1,916,085 | A | 6/1933 | Summers |
| 2,495,316 | A | 1/1950 | Clark |
| 3,929,129 | A | 12/1975 | Archambault |

(Continued)

FOREIGN PATENT DOCUMENTS

| | | |
|---|---|---|
| CN | 104955406 | 9/2015 |
| DE | 20305953 | 8/2003 |

(Continued)

OTHER PUBLICATIONS

Declaration of Aleksey Filippov, Apr. 23, 2007, 1 page.

(Continued)

*Primary Examiner* — Thomas McEvoy
(74) *Attorney, Agent, or Firm* — Fish & Richardson P.C.

(57) ABSTRACT

Rotational atherectomy devices and systems can remove or reduce stenotic lesions in blood vessels by rotating one or more abrasive elements within the vessel. The abrasive elements are attached to a distal portion of an elongate flexible drive shaft that extends from a handle assembly that includes a driver for rotating the drive shaft. In particular implementations, individual abrasive elements are attached to the drive shaft at differing radial angles in comparison to each other (e.g., configured in a helical array). The centers of mass of the abrasive elements can define a path that spirals around the drive shaft in a direction that is opposite to the wind direction of filars of the drive shaft, and opposite to the direction of rotation. In some embodiments, a concentric abrasive tip member is affixed to and extends distally from a distal-most end of the drive shaft.

30 Claims, 9 Drawing Sheets

(56) References Cited

U.S. PATENT DOCUMENTS

| | | |
|---|---|---|
| 4,445,509 A | 5/1984 | Auth |
| 4,445,892 A | 5/1984 | Auth |
| 4,620,320 A | 10/1986 | Sullivan |
| 4,646,736 A | 3/1987 | Auth |
| 4,784,636 A | 11/1988 | Rydell |
| 4,870,953 A | 10/1989 | DonMicheal |
| 4,931,635 A | 6/1990 | Toyama |
| 4,990,134 A | 2/1991 | Auth |
| 5,014,681 A | 5/1991 | Heeman |
| 5,100,425 A | 3/1992 | Fischell |
| 5,217,474 A | 6/1993 | Zacca |
| 5,242,460 A | 9/1993 | Klein |
| 5,250,059 A | 10/1993 | Andreas |
| 5,250,060 A | 10/1993 | Carbo |
| 5,273,526 A | 12/1993 | Dance |
| 5,308,354 A | 5/1994 | Zacca |
| 5,312,427 A | 5/1994 | Shturman |
| 5,314,407 A | 5/1994 | Auth |
| 5,314,438 A | 5/1994 | Shturman |
| 5,342,292 A | 8/1994 | Nita |
| 5,361,285 A | 11/1994 | Formanek |
| 5,370,653 A | 12/1994 | Cragg |
| 5,458,575 A | 10/1995 | Wang |
| 5,556,389 A | 9/1996 | Liprie |
| 5,584,843 A | 12/1996 | Wulfinan |
| 5,681,336 A | 10/1997 | Clement |
| 5,730,717 A | 3/1998 | Gelbfish |
| 5,816,923 A | 10/1998 | Milo |
| 5,843,103 A | 12/1998 | Wulfinan |
| 5,868,708 A | 2/1999 | Hart |
| 5,893,857 A | 4/1999 | Shturman |
| 6,010,533 A | 1/2000 | Pope |
| 6,022,363 A | 2/2000 | Walker |
| 6,024,749 A | 2/2000 | Shturman |
| 6,066,152 A | 5/2000 | Strauss |
| 6,077,282 A | 6/2000 | Shturman |
| 6,096,054 A | 8/2000 | Wyzgala |
| 6,132,444 A | 10/2000 | Shturman |
| 6,135,982 A | 10/2000 | Campbell |
| 6,146,395 A | 11/2000 | Hirst |
| 6,152,911 A | 11/2000 | Giannoble |
| 6,156,048 A | 12/2000 | Wulfman |
| 6,241,706 B1 | 6/2001 | Leschinsky |
| 6,270,465 B1 | 8/2001 | Keith |
| 6,491,660 B2 | 2/2002 | Guo |
| 6,416,526 B1 | 7/2002 | Hefner |
| 6,485,500 B1 | 11/2002 | Kokish |
| 6,494,890 B1 | 12/2002 | Shturman |
| 6,565,588 B1 | 5/2003 | Clement |
| 6,685,718 B1 | 2/2004 | Wyzgala |
| 6,733,513 B2 | 5/2004 | Boyle |
| 6,805,485 B2 | 10/2004 | Hogan |
| 6,852,118 B2 | 2/2005 | Shturman |
| 6,955,661 B1 | 10/2005 | Herweck |
| 8,109,954 B2 | 2/2012 | Shturman |
| 8,109,955 B2 | 2/2012 | Shturman |
| 8,137,369 B2 | 3/2012 | Shturman |
| 8,142,458 B2 | 3/2012 | Shturman |
| 8,147,507 B2 | 4/2012 | Shturman |
| 8,157,825 B2 | 4/2012 | Shturman |
| 8,177,801 B2 | 5/2012 | Kallok |
| 8,348,965 B2 | 1/2013 | Prudnikov |
| 8,353,923 B2 | 1/2013 | Shturman |
| 8,388,636 B2 | 3/2013 | Shturman |
| 8,388,637 B2 | 3/2013 | Shturman |
| 8,454,638 B2 | 6/2013 | Shturman |
| 8,465,510 B2 | 6/2013 | Shturman |
| 8,496,678 B2 | 7/2013 | Shturman |
| 8,500,764 B2 | 8/2013 | Shturman |
| 8,500,765 B2 | 8/2013 | Shturman |
| 8,628,550 B2 | 1/2014 | Narveson |
| 8,663,195 B2 | 3/2014 | Shturman |
| 8,663,260 B2 | 3/2014 | Shturman |
| 8,663,261 B2 | 3/2014 | Shturman |
| 9,289,230 B2 | 3/2016 | Cambronne |
| 9,387,006 B2 | 7/2016 | Shturman |
| 10,052,122 B2 | 8/2018 | Higgins |
| 10,052,124 B2 | 8/2018 | Cambronne |
| 10,064,646 B2 | 9/2018 | Cambronne |
| 2002/0007190 A1 | 1/2002 | Wulfman |
| 2002/0082547 A1 | 6/2002 | Deniega |
| 2002/0099367 A1 | 7/2002 | Guo |
| 2002/0138088 A1 | 9/2002 | Nash |
| 2002/0188276 A1 | 12/2002 | Guo |
| 2003/0199889 A1 | 10/2003 | Kanz |
| 2004/0098014 A1 | 5/2004 | Flugelman |
| 2004/0158270 A1 | 8/2004 | Wyzgala |
| 2005/0154416 A1 | 7/2005 | Herweck |
| 2005/0209615 A1 | 9/2005 | Prudnikov |
| 2005/0240146 A1 | 10/2005 | Nash |
| 2005/0256461 A1 | 11/2005 | DiFiore |
| 2007/0066888 A1 | 3/2007 | Maschke |
| 2008/0097498 A1 | 4/2008 | Shimizu |
| 2008/0161840 A1 | 7/2008 | Osiroff |
| 2008/0319415 A1 | 12/2008 | Shturman |
| 2009/0018564 A1 | 1/2009 | Shturman |
| 2009/0069829 A1 | 3/2009 | Shturman |
| 2009/0105736 A1 | 4/2009 | Kawakubo |
| 2009/0182359 A1 | 7/2009 | Shturman |
| 2009/0312777 A1 | 12/2009 | Shturman |
| 2009/0318942 A1 | 12/2009 | Shturman |
| 2009/0326568 A1 | 12/2009 | Shturman |
| 2010/0010522 A1 | 1/2010 | Shturman |
| 2010/0049226 A1 | 2/2010 | Shturman |
| 2010/0121361 A1 | 5/2010 | Plowe |
| 2011/0009888 A1 | 1/2011 | Shturman |
| 2011/0054332 A1 | 3/2011 | Shturman |
| 2012/0035633 A1 | 2/2012 | Shturman |
| 2012/0109170 A1 | 5/2012 | Shturman |
| 2012/0150207 A1 | 6/2012 | Shturman |
| 2012/0178986 A1 | 7/2012 | Campbell |
| 2012/0191113 A1 | 7/2012 | Shturman |
| 2012/0213391 A1 | 8/2012 | Usami |
| 2013/0178881 A1 | 7/2013 | Shturman |
| 2013/0245654 A1 | 9/2013 | Shturman |
| 2013/0274773 A1 | 10/2013 | Shturman |
| 2013/0296904 A1 | 11/2013 | Shturman |
| 2013/0296905 A1 | 11/2013 | Shturman |
| 2013/0310589 A1 | 11/2013 | Shturman |
| 2014/0081298 A1 | 3/2014 | Cambronne |
| 2015/0080795 A1 | 3/2015 | Mattison |
| 2015/0196320 A1 | 7/2015 | Robinson |
| 2016/0346003 A1 | 12/2016 | Grothe |
| 2017/0056040 A1 | 3/2017 | Vetter |
| 2017/0290603 A1 | 10/2017 | Piippo |
| 2018/0235652 A1 | 8/2018 | Benjamin |
| 2018/0263654 A1 | 9/2018 | Steele |

FOREIGN PATENT DOCUMENTS

| | | |
|---|---|---|
| EP | 0419154 | 3/1991 |
| EP | 0820729 | 1/1998 |
| EP | 1405797 | 4/2004 |
| EP | 1820458 | 8/2007 |
| FR | 1595757 | 6/1970 |
| GB | 854573 | 11/1960 |
| GB | 2039208 | 8/1980 |
| GB | 2357573 | 6/2001 |
| GB | 2426458 | 11/2006 |
| WO | WO 199850101 | 11/1998 |
| WO | WO 199944513 | 9/1999 |
| WO | WO 2001015759 | 3/2001 |
| WO | WO 2002009599 | 2/2002 |
| WO | WO 2006126076 | 11/2006 |
| WO | WO 2006126175 | 11/2006 |
| WO | WO 2006126176 | 11/2006 |
| WO | WO 2014042752 | 3/2014 |

OTHER PUBLICATIONS

Declaration of Dmitri Prudnikov, Apr. 23, 2007, 1 page.
Excerpt from Deposition of Dmitri Prudnikov, Mar. 5, 2008, 7 pages.

(56) References Cited

OTHER PUBLICATIONS

Excerpt from Deposition of Dmitri Prudnikov, Mar. 6, 2008, 54 pages.
Exhibits Nos. 14, 31 & 32, from Deposition of Dmitri Prudnikov, Mar. 5, 2008, 3 pages.
Exhibits Nos. 33-39 from Deposition of Dmitri Prudnikov, Mar. 6, 2008, 47 pages.
International Search Report, corresponding to Int'l Application No. PCT/US2015/011212, dated May 6, 2015.
International Search Report and Written Opinion in International Application No. PCT/US2018/019238, dated May 8, 2018, 16 pages.
"Declaration of Dr. Morten Olgaard Jensen," IPR2018-01549, Exhibit 1002, dated Aug. 15, 2018.
"Petition for Inter Partes Review of U.S. Pat. No. 9,788,853 Under 35 U.S.C. § 312 and 37 C.F.R. § 42.104," *Cardiovascular Systems, Inc.* v. *Cardio Flow, Inc.*, IPR2018-01549, Paper 1, dated Aug. 17, 2018.
"Declaration of Kristina Rouw, Ph.D," IPR2018-01549, Exhibit 2001, dated Nov. 29, 2018.
"Patent Owner's Preliminary Response," IPR2018-01549, Paper 8, dated Nov. 29, 2018.
"Declaration of Dr. Morten Olgaard Jensen," IPIPR2018-01658, Exhibit 1002, dated Sep. 4, 2018.
"Declaration of Kristina Rouw, Ph.D," IPR2018-01658, Exhibit 2001, dated Dec. 10, 2018.
"Petition for Inter Partes Review of U.S. Pat. No. 9,089,362 Under 35 U.S.C. § 312 and 37 C.F.R. § 42.104," *Cardiovascular Systems, Inc.* v. *Cardio Flow, Inc.*, IPR2018-01658, Paper 1, dated Sep. 5, 2018.
"Patent Owner's Preliminary Response," IPR2018-01658, Paper 6, dated Dec. 11, 2018.

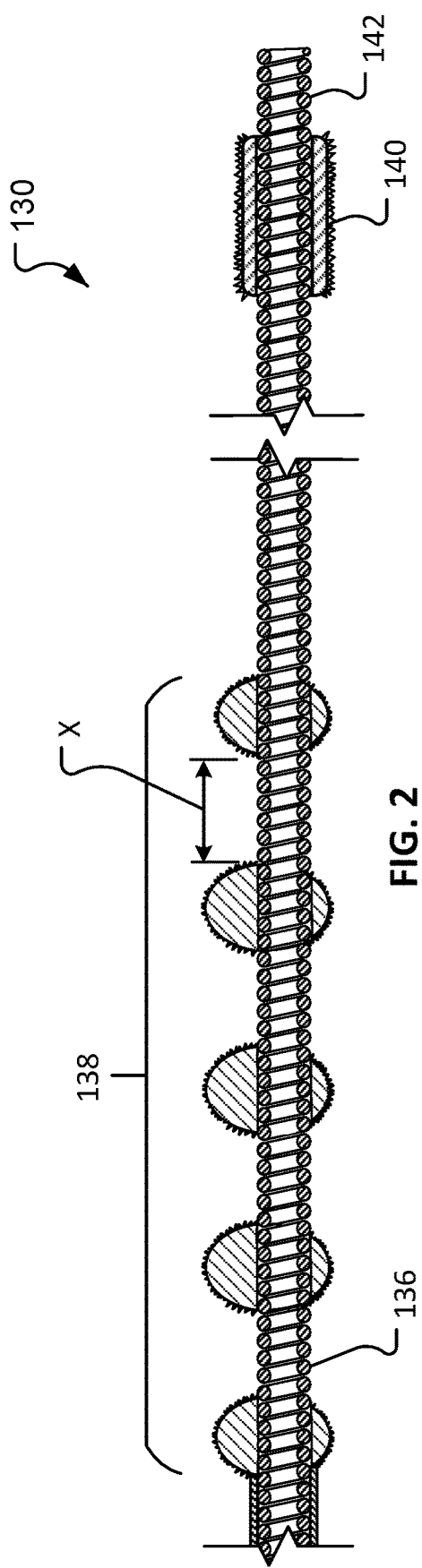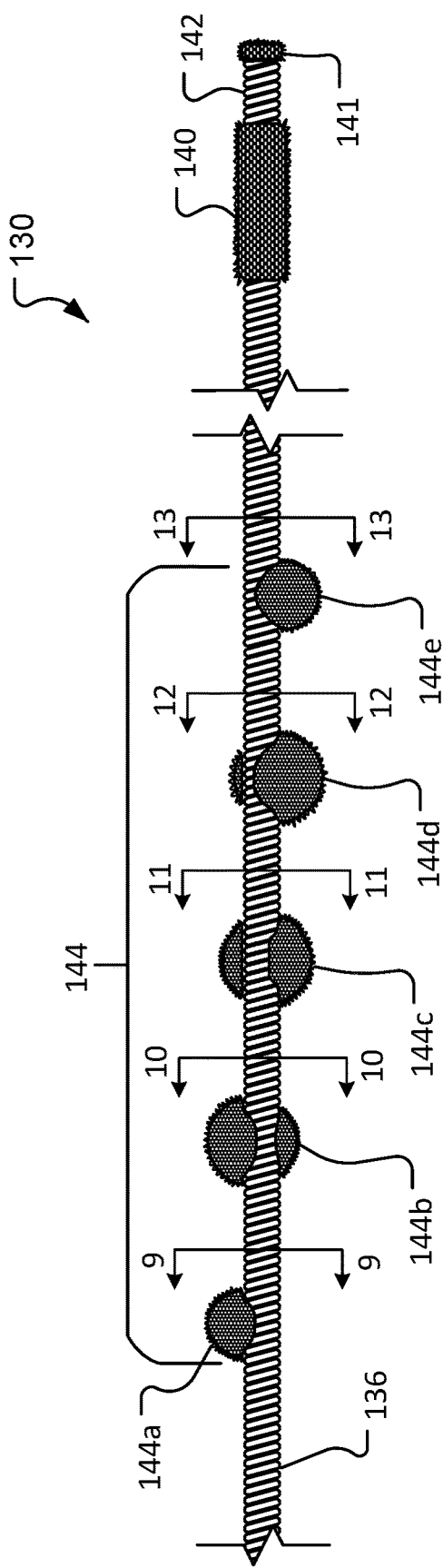

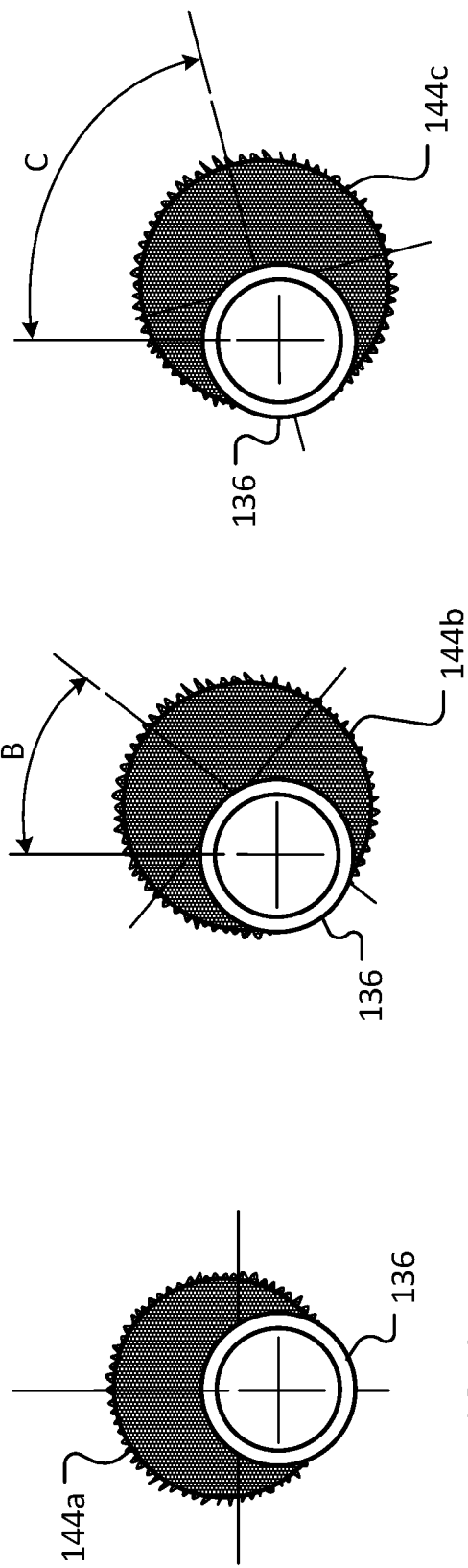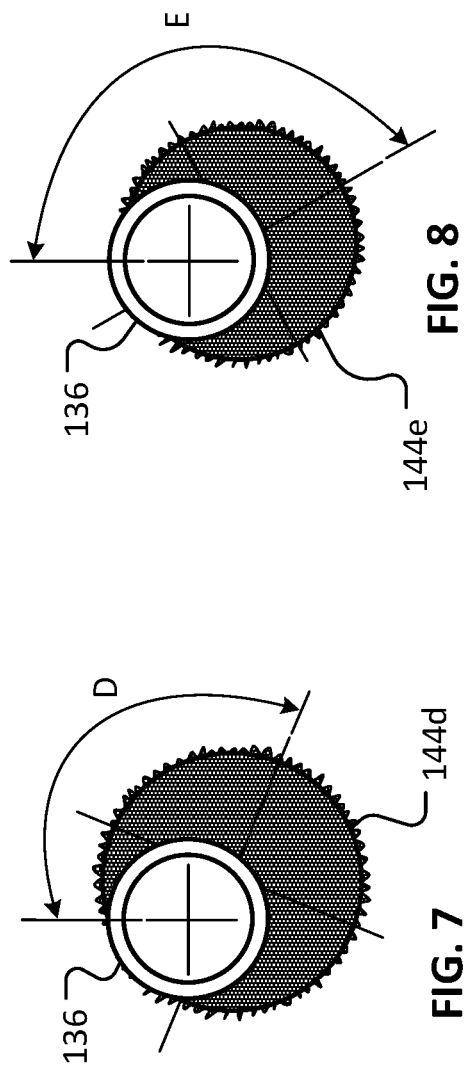

ATHERECTOMY DEVICES AND METHODS

CLAIM OF PRIORITY

This application is a continuation which claims priority to U.S. patent application Ser. No. 16/146,809, filed on Sep. 28, 2018, which is a continuation of U.S. patent application Ser. No. 15/988,160, filed on May 24, 2018, the entire contents of which are hereby incorporated by reference.

TECHNICAL FIELD

This document relates to rotational atherectomy devices and systems for removing or reducing stenotic lesions in blood vessels, for example, by rotating an abrasive element within the vessel to partially or completely remove the stenotic lesion material.

BACKGROUND

Atherosclerosis, the clogging of arteries with plaque, is often a result of coronary heart disease or vascular problems in other regions of the body. Plaque is made up of fat, cholesterol, calcium, and other substances found in the blood. Over time, the plaque hardens and narrows the arteries. This limits the flow of oxygen-rich blood to organs and other parts of the body.

Blood flow through the central and peripheral arteries (e.g., carotid, iliac, femoral, renal etc.), can be similarly affected by the development of atherosclerotic blockages. Peripheral artery disease (PAD) can be serious because without adequate blood flow, the kidneys, legs, arms, and feet may suffer irreversible damage. Left untreated, the tissue can die or harbor infection.

One method for removing or reducing such blockages in blood vessels is known as rotational atherectomy. In some implementations, a drive shaft carrying an abrasive burr or other abrasive surface (e.g., formed from diamond grit or diamond particles) rotates at a high speed within the vessel, and the clinician operator slowly advances the atherectomy device distally so that the abrasive burr scrapes against the occluding lesion and grinds it into very small particles, reducing the occlusion and improving blood flow through the vessel.

SUMMARY

Some embodiments of rotational atherectomy systems described herein can remove or reduce stenotic lesions in blood vessels by rotating one or more abrasive elements in an orbital path to abrade and breakdown the lesion. In some embodiments, the abrasive element(s) are eccentrically attached to a distal portion of an elongate flexible drive shaft that extends from a handle assembly. In particular embodiments, multiple abrasive elements are coupled to the drive shaft and are offset from each other around the drive shaft such that the centers of mass of the abrasive elements are disposed at differing radial angles from the drive shaft in relation to each other. For example, in some embodiments a path defined by the centers of mass of the abrasive elements defines a spiral around a length of the central longitudinal axis of the drive shaft. In some embodiments, the rotational atherectomy systems described herein are used by rotating the drive shaft around the longitudinal axis in a direction opposite of the spiral path defined by the centers of mass of the abrasive elements. In particular embodiments, the drive shaft is constructed of one or more helically-wound filars that are wound in a direction opposite to the spiral path defined by the centers of mass of the abrasive elements and in the same direction as the drive shaft's rotation during use. Also, in some optional embodiments, a tip member with an abrasive surface is affixed to the distal-most end of the drive shaft such that the abrasive tip member extends distally of the drive shaft.

In one aspect, this disclosure is directed to a rotational atherectomy device for removing stenotic lesion material from a blood vessel of a patient. In some embodiments, the rotational atherectomy device includes an elongate flexible drive shaft and two or more abrasive elements attached to a distal end portion of the drive shaft. The elongate flexible drive shaft defines a longitudinal axis and includes a torque-transmitting coil of one or more filars that are helically wound around the longitudinal axis in a first spiral direction. Each of the two or more abrasive elements have a center of mass that is offset from the longitudinal axis. The center of mass of a first abrasive element of the abrasive elements is offset from the longitudinal axis at a first radial angle, and the center of mass of a second abrasive element of the abrasive elements is offset from the longitudinal axis at a second radial angle that differs from the first radial angle. A path defined by the centers of mass of the first and second abrasive elements spirals around the longitudinal axis in a second spiral direction that is opposite of the first spiral direction (of the drive shaft).

Such a rotational atherectomy device for removing stenotic lesion material from a blood vessel of a patient may optionally include one or more of the following features. may optionally include one or more of the following features. When viewed in a distal direction from a proximal end of the drive shaft, the first spiral direction may be clockwise and the second spiral direction may be counterclockwise. When viewed in a distal direction from a proximal end of the drive shaft, the first spiral direction may be counterclockwise and the second spiral direction may be clockwise. The rotational atherectomy device may also include a third abrasive element attached to the distal end portion of the drive shaft. The center of mass of the third abrasive element may be offset from the longitudinal axis along a third radial angle that differs from the first radial angle and the second radial angle. In some embodiments, the second radial angle differs from the first radial angle by at least 15 degrees, and the third radial angle differs from the first radial angle and the second radial angle by at least 15 degrees. The rotational atherectomy device may include at least four abrasive elements attached to the distal end portion of the drive shaft. Each of the at least four abrasive elements may have a center of mass offset from the longitudinal axis. A spiral path defined by the centers of mass of the at least four abrasive elements may spiral around the longitudinal axis. An overall radial angle of the spiral path may be defined by a radial angle between a distal-most abrasive element of the at least four abrasive elements and a proximal-most abrasive element of the at least four abrasive elements. In some embodiments, the overall radial angle of the spiral path is always less than 180 degrees along any 10 cm length of the distal end portion of the drive shaft. The rotational atherectomy device may also include an actuator handle assembly configured to drive rotation of the drive shaft about the longitudinal axis. The actuator handle assembly may include a carriage assembly that is movable in relation to other portions of the actuator handle assembly to translate the drive shaft along the longitudinal axis. The rotational atherectomy device may also include a sheath extending from the actuator handle assembly. The drive shaft may be slidably disposed within a lumen defined by the sheath. In some embodiments, the drive shaft includes a distal-most extension portion that extends distally of a distal-most abrasive element of the abrasive elements. The rotational atherectomy device may also include a concentric abrasive tip member affixed to and extending distally from a distal-most end of the distal-most extension portion. The tip member may have an abrasive material on an exterior surface of the tip member.

In another aspect, this disclosure is directed to a method for performing rotational atherectomy to remove stenotic lesion material from a blood vessel of a patient. The method includes delivering a rotational atherectomy device into the blood vessel. Such a rotational atherectomy device can include: (i) an elongate flexible drive shaft defining a longitudinal axis and comprising a torque-transmitting coil of one or more filars that are helically wound around the longitudinal axis in a first spiral direction, and (ii) two or more abrasive elements attached to a distal end portion of the drive shaft and each having a center of mass offset from the longitudinal axis. A path defined by the centers of mass of the first and second abrasive elements spirals around the longitudinal axis in a second spiral direction that is opposite of the first spiral direction. The method for performing rotational atherectomy to remove stenotic lesion material from a blood vessel of a patient also includes rotating the drive shaft about the longitudinal axis in the first spiral direction such that the abrasive elements orbit around the longitudinal axis.

Such a method for performing rotational atherectomy to remove stenotic lesion material from a blood vessel of a patient may optionally include one or more of the following features. When viewed in a distal direction from a proximal end of the drive shaft, the first spiral direction may be clockwise and the second spiral direction may be counter-clockwise. When viewed in a distal direction from a proximal end of the drive shaft, the first spiral direction may be counterclockwise and the second spiral direction may be clockwise. The rotational atherectomy may be performed without using a lubricant between the drive shaft and a guidewire that is disposed within a lumen defined by the drive shaft.

In another aspect, this disclosure is directed to another method for performing rotational atherectomy to remove stenotic lesion material from a blood vessel of a patient. The method includes delivering a rotational atherectomy device into the blood vessel. The rotational atherectomy device includes: (a) an elongate flexible drive shaft defining a longitudinal axis and comprising a torque-transmitting coil of one or more filars that are helically wound around the longitudinal axis in a first spiral direction; and (b) two or more abrasive elements attached to a distal end portion of the drive shaft and each having a center of mass offset from the longitudinal axis. The center of mass of a first abrasive element of the abrasive elements is offset from the longitudinal axis at a first radial angle, and the center of mass of a second abrasive element of the abrasive elements is offset from the longitudinal axis at a second radial angle that differs from the first radial angle. The method for performing rotational atherectomy to remove stenotic lesion material from a blood vessel of a patient also includes rotating the drive shaft about the longitudinal axis in the first spiral direction such that the abrasive elements orbit around the longitudinal axis.

Such a method for performing rotational atherectomy to remove stenotic lesion material from a blood vessel of a patient may optionally include one or more of the following features. When viewed in a distal direction from a proximal end of the drive shaft, the first spiral direction may be clockwise and the second spiral direction may be counter-clockwise. When viewed in a distal direction from a proximal end of the drive shaft, the first spiral direction may be counterclockwise and the second spiral direction may be clockwise.

In another aspect, this disclosure is directed to a rotational atherectomy device for removing stenotic lesion material from a blood vessel of a patient. The rotational atherectomy device includes: (1) an elongate flexible drive shaft defining a longitudinal axis and comprising a torque-transmitting coil; (2) a set of eccentric abrasive elements attached to a distal end portion of the drive shaft and each having a center of mass offset from the longitudinal axis; and (3) a concentric abrasive tip member affixed to and extending distally from a distal-most end of the drive shaft. The tip member includes an abrasive material along an exterior circumferential surface having a maximum lateral width smaller than a maximum lateral width of each of the eccentric abrasive elements.

Such a rotational atherectomy device for removing stenotic lesion material from a blood vessel of a patient may optionally include one or more of the following features. The set of eccentric abrasive elements may include two or more abrasive elements. The center of mass of a first abrasive element of the abrasive elements may be offset from the longitudinal axis at a first radial angle, and the center of mass of a second abrasive element of the abrasive elements may be offset from the longitudinal axis at a second radial angle that differs from the first radial angle. The set of eccentric abrasive elements may include at least four abrasive elements. A spiral path defined by the centers of mass of the at least four abrasive elements may spiral around the longitudinal axis. An overall radial angle of the spiral path may be defined by a radial angle between a distal-most abrasive element of the at least four abrasive elements and a proximal-most abrasive element of the at least four abrasive elements. In some embodiments, the overall radial angle of the spiral path is always less than 180 degrees along any 10 cm length of the distal end portion of the drive shaft.

In another aspect, this disclosure is directed to another rotational atherectomy device for removing stenotic lesion material from a blood vessel of a patient. The device includes an elongate flexible drive shaft defining a longitudinal axis and comprising a torque-transmitting coil (the drive shaft configured to rotate about the longitudinal axis), and at least four abrasive elements attached to a distal end portion of the drive shaft and each having a center of mass offset from the longitudinal axis. A spiral path defined by the centers of mass of the at least four abrasive elements spirals around the longitudinal axis. An overall radial angle of the spiral path is defined by a radial angle between a distal-most abrasive element of the at least four abrasive elements and a proximal-most abrasive element of the at least four abrasive elements. In some embodiments, the overall radial angle of the spiral path is always less than 180 degrees along any 10 cm length of the distal end portion of the drive shaft.

Such a rotational atherectomy device for removing stenotic lesion material from a blood vessel of a patient may optionally include one or more of the following features. The torque-transmitting coil may include one or more filars that are helically wound around the longitudinal axis in a spiral direction that is opposite in comparison to the spiral path defined by the centers of mass of the at least four abrasive elements.

Some of the embodiments described herein may provide one or more of the following advantages. First, some embodiments of the rotational atherectomy system include a drive shaft constructed of one or more helically wound filars that are wound in the same direction that the drive shaft is rotated during use. Accordingly, the turns of the helically wound filars can tend to radially expand and separate from each other (or "open up") during rotational use. Such a scenario advantageously reduces frictional losses between adjacent filar turns. Additionally, when a guidewire is disposed within the lumen defined by the helically wound filars during rotational use, the drive shaft will tend to loosen on the guidewire rather than to tighten on it. Consequently, in some cases no use of lubricant between the guidewire and the drive shaft is necessary. Moreover, since the drive shaft will tend to loosen on the guidewire, less stress will be induced on the guidewire during rotation of the drive shaft. Thus, the potential for causing breaks of the guidewire is advantageously reduced. Further, since the drive shaft will tend to loosen on the guidewire during use, a larger guidewire can be advantageously used in some cases.

Second, some embodiments of the rotational atherectomy devices and systems provided herein include multiple abrasive elements that are offset from each other around the drive shaft such that the centers of mass of the abrasive elements define a path that spirals around a central longitudinal axis of the drive shaft. In particular embodiments, the rotational atherectomy systems are used by rotating the drive shaft around the longitudinal axis in a direction opposite of the spiral path defined by the centers of mass of the abrasive elements. Such an arrangement can advantageously provide a smoother running and more controllable atherectomy procedure as compared to systems that rotate the drive shaft in the same direction as the spiral path defined by the centers of mass of the abrasive elements.

Third, some embodiments of the rotational atherectomy devices and systems described herein include a tip member with an abrasive surface is affixed to the distal-most end of the drive shaft such that the abrasive tip member extends distally on the drive shaft. In some cases, while the rotational atherectomy device is being advanced within the vasculature of a patient, the distal end of the rotational atherectomy device may encounter lesions that occlude or substantially occlude the vessel. In such a case, the abrasive outer surface on the distal tip member may help facilitate passage of the drive shaft through lesions that occlude or substantially occlude the vessel. In some such cases, the drive shaft may be used to rotate the abrasive tip member to help facilitate boring of the drive shaft through such lesions in a drill-like fashion.

Fourth, in some embodiments of the rotational atherectomy devices and systems that include multiple abrasive elements that are offset such that the centers of mass of the abrasive elements define a path that spirals around a central longitudinal axis of the drive shaft, the radial angles of the abrasive elements differ by not more than 180° along any 10 cm length of the drive shaft. Such a design can advantageously assist the eccentric abrasive elements to consistently orbit around a predictable, predefined path and minimize the profile such that the abrasive elements can be advanced through a suitably small-sized introducer sheath.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a longitudinal cross-sectional view of a distal portion of an example rotational atherectomy device showing a multi-portion abrasive element and a distal stability element with an abrasive coating.

FIG. 3 is a side view of a distal portion of another example rotational atherectomy device showing a multi-portion abrasive element and a distal stability element with an abrasive coating. The individual portions of the multi-portion abrasive element are offset from each other around the drive shaft such that the centers of mass of the abrasive element portions define a spiral path around the drive shaft axis.

FIG. 4 is a transverse cross-sectional view of the rotational atherectomy device of FIG. 3 taken along the cutting-plane line 9-9.

FIG. 5 is a transverse cross-sectional view of the rotational atherectomy device of FIG. 3 taken along the cutting-plane line 10-10.

FIG. 6 is a transverse cross-sectional view of the rotational atherectomy device of FIG. 3 taken along the cutting-plane line 11-11.

FIG. 7 is a transverse cross-sectional view of the rotational atherectomy device of FIG. 3 taken along the cutting-plane line 12-12.

FIG. 8 is a transverse cross-sectional view of the rotational atherectomy device of FIG. 3 taken along the cutting-plane line 13-13.

Like reference symbols in the various drawings indicate like elements.

DETAILED DESCRIPTION OF ILLUSTRATIVE EMBODIMENTS

Figure 1:
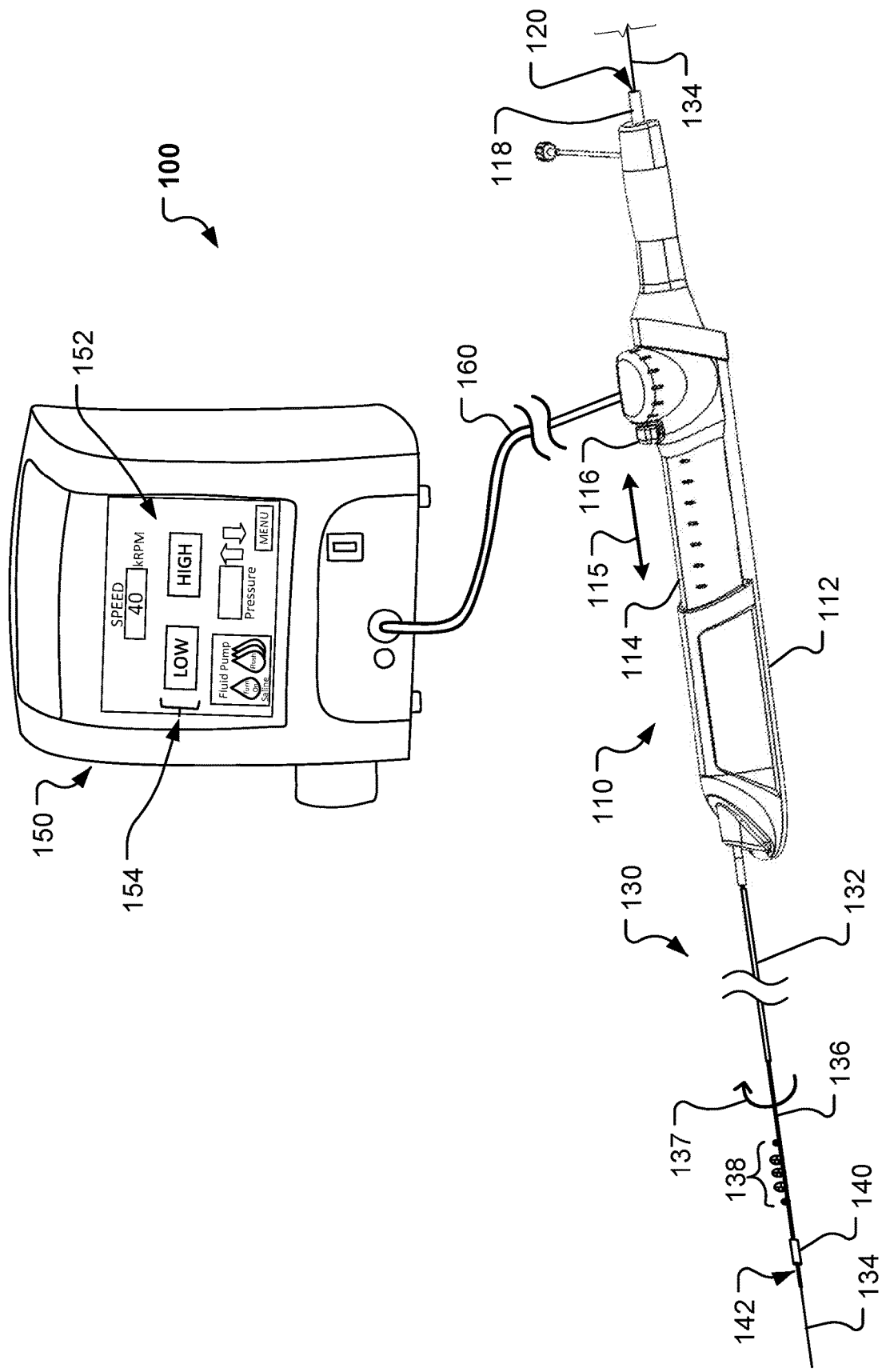
FIG. 1 is a perspective view of an example rotational atherectomy system in accordance with some embodiments.

Referring to FIG. 1, in some embodiments a rotational atherectomy system 100 for removing or reducing stenotic lesions in blood vessels can include a guidewire 134, an actuator handle assembly 110, an elongate flexible drive shaft assembly 130, and a controller 150. The drive shaft assembly 130 extends distally from the handle assembly 110. The controller 150 is connected to the handle assembly 110 via a cable assembly 160. The handle assembly 110 and controller 150 can be operated by a clinician to perform and control the rotational atherectomy procedure.

In the depicted embodiment, the elongate flexible drive shaft assembly 130 includes a sheath 132 and a flexible drive shaft 136. A proximal end of the sheath 132 is fixed to a distal end of the handle assembly 110. The flexible drive shaft 136 is slidably and rotatably disposed within a lumen of the sheath 132. The flexible drive shaft 136 defines a longitudinal lumen in which the guidewire 134 is slidably disposed. In this embodiment, the flexible drive shaft 136 includes a torque-transmitting coil of one or more helically wound filars that defines the longitudinal lumen along a central longitudinal axis. The drive 136 shaft is configured to rotate about the longitudinal axis while the sheath 132 remains generally stationary. Hence, as described further below, during a rotational atherectomy procedure the flexible drive shaft 136 is in motion (e.g., rotating about the longitudinal axis and periodically longitudinally translating proximally and/or distally) while the sheath 132 and the guidewire 134 are generally stationary.

In some optional embodiments, an inflatable member (not shown) can surround a distal end portion of the sheath 132. Such an inflatable member can be selectively expandable between a deflated low-profile configuration and an inflated deployed configuration. The sheath 132 may define an inflation lumen through which the inflation fluid can pass (to and from the optional inflatable member). The inflatable member can be in the deflated low-profile configuration during the navigation of the drive shaft assembly 130 through the patient's vasculature to a target location in a vessel. Then, at the target location, the inflatable member can be inflated so that the outer diameter of the inflatable member contacts the wall of the vessel. In that arrangement, the inflatable member advantageously stabilizes the drive shaft assembly 130 in the vessel during the rotational atherectomy procedure.

Still referring to FIG. 1, the flexible driveshaft 136 is slidably and rotatably disposed within a lumen of the sheath 132. A distal end portion of the driveshaft 136 extends distally of the distal end of the sheath 132 such that the distal end portion of the driveshaft 136 is exposed (e.g., not within the sheath 132, at least not during the performance of the actual rotational atherectomy).

In the depicted embodiment, the exposed distal end portion of the driveshaft 136 includes one or more abrasive elements 138, a (optional) distal stability element 140, a distal drive shaft extension portion 142, and a (optional) concentric abrasive tip member 141 (refer to FIG. 3). In the depicted embodiment, the one or more abrasive elements 138 are eccentrically-fixed to the driveshaft 136 proximal of the optional distal stability element 140. In this embodiment, the distal stability element 140 is concentrically-fixed to the driveshaft 136 between the one or more abrasive elements 138 and the distal drive shaft extension portion 142. As such, the center of mass of the distal stability element 140 is aligned with the central axis of the drive shaft 136 while the center of mass of each abrasive element 138 is offset from the central axis of the drive shaft 136. The distal drive shaft extension portion 142 (which is part of the drive shaft 136 and is constructed of the torque-transmitting coil made up of one or more helically wound filars) is configured to rotate about the longitudinal axis. The distal drive shaft extension portion 142 extends distally from the distal stability element 140 and terminates at a free end of the drive shaft 136. In some embodiments, a concentric abrasive tip member 141 (refer to FIG. 3) is affixed to, and extends distally from, the terminal distal-most end of the distal drive shaft extension portion 142. It can also be said that the concentric abrasive tip member 141 is affixed to, and extends distally from, the drive shaft 136.

In some optional embodiments, a proximal stability element (not shown) is included. The proximal stability element can be constructed and configured similarly to the depicted embodiment of the distal stability element 140 (e.g., a metallic cylinder directly coupled to the torque-transmitting coil of the drive shaft 136 and concentric with the longitudinal axis of the drive shaft 136) while being located proximal to the one or more abrasive elements 138.

In the depicted embodiment, the distal stability element 140 has a center of mass that is axially aligned with a central longitudinal axis of the drive shaft 136, while the one or more abrasive elements 138 (collectively and/or individually) have a center of mass that is axially offset from central longitudinal axis of the drive shaft 136. Accordingly, as the drive shaft 136 is rotated about its longitudinal axis, the principle of centrifugal force will cause the one or more abrasive elements 138 (and the portion of the drive shaft 136 to which the one or more abrasive elements 138 are affixed) to follow a transverse generally circular orbit (e.g., somewhat similar to a "jump rope" orbital movement) relative to the central axis of the drive shaft 136 (as described below, for example, in connection with FIGS. 15-17). In general, faster speeds (rpm) of rotation of the drive shaft 136 will result in larger diameters of the orbit (within the limits of the vessel diameter). The orbiting one or more abrasive elements 138 will contact the stenotic lesion to ablate or abrade the lesion to a reduced size (i.e., small particles of the lesion will be abraded from the lesion).

The rotating distal stability element 140 will remain generally at the longitudinal axis of the drive shaft 136 as the drive shaft 136 is rotated (as described below, for example, in connection with FIGS. 15-17). In some optional embodiments, two or more distal stability elements 140 are included. As described further below, contemporaneous with the rotation of the drive shaft 136, the drive shaft 136 can be translated back and forth (distally and proximally) along the longitudinal axis of the drive shaft 136. Hence, lesions can be abraded radially and longitudinally by virtue of the orbital rotation and translation of the one or more abrasive elements 138, respectively.

The flexible drive shaft 136 of rotational atherectomy system 100 is laterally flexible so that the drive shaft 136 can readily conform to the non-linear vasculature of the patient, and so that a portion of the drive shaft 136 at, and adjacent to, the one or more abrasive elements 138 will laterally deflect when acted on by the centrifugal forces resulting from the rotation of the one or more eccentric abrasive elements 138. In this embodiment, the drive shaft 136 comprises one or more helically wound wires (or filars) that provide one or more torque-transmitting coils of the drive shaft 136 (as described further below, for example, in connection with FIGS. 2 and 3).

In some embodiments, the one or more helically wound wires (filars) of the drive shaft 136 are made of a metallic material such as, but not limited to, stainless steel (e.g., 316, 316L, or 316LVM), nitinol, titanium, titanium alloys (e.g., titanium beta 3), carbon steel, or another suitable metal or metal alloy. In some alternative embodiments, the filars are or include graphite, Kevlar, or a polymeric material. In some embodiments, the filars can be woven, rather than wound. In some embodiments, individual filars can comprise multiple strands of material that are twisted, woven, or otherwise coupled together to form a filar. In some embodiments, the filars have different cross-sectional geometries (size or shape) at different portions along the axial length of the drive shaft 136. In some embodiments, the filars have a cross-sectional geometry other than a circle, e.g., an ovular, square, triangular, or another suitable shape.

Any suitable number of individual filars can be included to construct the drive shaft 136. For example, in some embodiments one, two, three, four, five, six, seven, eight, nine, ten, eleven, twelve, thirteen, fourteen, fifteen, or more than fifteen individual filars can be helically wound among each other to make up the drive shaft 136. As described further below, the direction in which the filars of the drive shaft 136 are wound is a design feature that can be selected to obtain desirable, advantageous operational characteristics. For example, it can be desirable to select the direction in which the filars of the drive shaft 136 are wound in relation to: (i) the direction of rotation of the drive shaft 136 during use, and/or (ii) the direction of a path defined by the centers of mass of eccentric abrasive elements that spirals around the longitudinal axis of the drive shaft 136.

When a drive shaft that is constructed of one or more helically wound filars (e.g., the drive shaft 136) is rotated about its central longitudinal axis, depending on the direction of rotation in relation to the direction the filars are wound, the helically wound filars will either tend to radially expand ("open up") or radially contract. For example, when the direction of rotation and the direction the filars are wound are the same direction, the winds of the filars will tend to radially expand (the drive shaft will tend to "open up"). Conversely, when the direction of rotation and the direction the filars are wound are in opposite directions, the winds of the filars will tend to radially contract. While the rotational atherectomy system 100 described herein can be operated in either manner, the inventors have discovered that advantageous operational results can be obtained when the direction of rotation and the direction the filars are wound are the same direction, (that is, when the winds of the filars will tend to radially expand or "open up"). For example, such a scenario advantageously reduces frictional losses between adjacent filar turns/winds. Additionally, when the guidewire 134 is disposed within the lumen defined by the helically wound filars during use, the drive shaft 136 will tend to loosen on the guidewire 134 rather than to tighten on it. Consequently, in some cases no use of lubricant (e.g., an oil-based or biological lubricant) between the guidewire 134 and the drive shaft 136 is necessary. In this context, saline solutions are not considered to be a lubricant, but rather a coolant. Moreover, since the drive shaft 136 will tend to loosen on the guidewire 134, less stress will be induced on the guidewire 134 during rotation of the drive shaft 136. Thus, the potential for causing breaks of the guidewire 134 is advantageously reduced. Further, since the drive shaft 136 will tend to loosen on the guidewire 134 during use, a larger guidewire 134 can be advantageously used in some cases.

In this embodiment, the drive shaft 136 has a hollow core. That is, the drive shaft 136 defines a central longitudinal lumen running therethrough. The lumen can be used to slidably receive the guidewire 134 therein, as will be described further below. In some embodiments, the lumen can be used to aspirate particulate or to convey fluids that are beneficial for the atherectomy procedure.

In some embodiments, the drive shaft 136 includes an optional coating on one or more portions of the outer diameter of the drive shaft 136. The coating may also be described as a jacket, a sleeve, a covering, a casing, and the like. In some embodiments, the coating adds column strength to the drive shaft 136 to facilitate a greater ability to push the drive shaft 136 through stenotic lesions. In addition, the coating can enhance the rotational stability of the drive shaft 136 during use. In some embodiments, the coating is a flexible polymer coating that surrounds an outer diameter of the coil (but not the abrasive elements 138 or the distal stability element 140) along at least a portion of drive shaft 136 (e.g., the distal portion of the drive shaft 136 exposed outwardly from the sheath 132). In some embodiments, a portion of the drive shaft 136 or all of the drive shaft 136 is uncoated. In particular embodiments, the coating is a fluid impermeable material such that the lumen of the drive shaft 136 provides a fluid impermeable flow path along at least the coated portions of the drive shaft 136.

The coating may be made of materials including, but not limited to, PEBEX, PICOFLEX, PTFE, ePTFE, FEP, PEEK, silicone, PVC, urethane, polyethylene, polypropylene, and the like, and combinations thereof. In some embodiments, the coating covers the distal stability element 140 and the distal extension portion 142, thereby leaving only the one or more abrasive elements 138 exposed (non-coated) along the distal portion of the drive shaft 136. In alternative embodiments, the distal stability element 140 is not covered with the coating, and thus would be exposed like the abrasive element 140. In some embodiments, two or more layers of the coating can be included on portions of the drive shaft 136. Further, in some embodiments different coating materials (e.g., with different durometers and/or stiffnesses) can be used at different locations on the drive shaft 136.

In the depicted embodiment, the optional distal stability element 140 is a metallic cylindrical member having an inner diameter that surrounds a portion of the outer diameter of the drive shaft 136. In some embodiments, the distal stability element 140 has a longitudinal length that is greater than a maximum exterior diameter of the distal stability element 140. In the depicted embodiment, the distal stability element 140 is coaxial with the longitudinal axis of the drive shaft 136. Therefore, the center of mass of the distal stability element 140 is axially aligned (non-eccentric) with the longitudinal axis of the drive shaft 136. In alternative rotational atherectomy device embodiments, stability element(s) that have centers of mass that are eccentric in relation to the longitudinal axis may be included in addition to, or as an alternative to, the coaxial stability elements 140. For example, in some alternative embodiments, the stability element(s) can have centers of mass that are eccentric in relation to the longitudinal axis and that are offset 180 degrees (or otherwise oriented) in relation to the center of mass of the one or more abrasive elements 138.

The distal stability element 140 may be made of a suitable biocompatible material, such as a higher-density biocompatible material. For example, in some embodiments the distal stability element 140 may be made of metallic materials such as stainless steel, tungsten, molybdenum, iridium, cobalt, cadmium, and the like, and alloys thereof. The distal stability element 140 has a fixed outer diameter. That is, the distal stability element 140 is not an expandable member in the depicted embodiment. The distal stability element 140 may be mounted to the filars of the drive shaft 136 using a biocompatible adhesive, by welding, by press fitting, and the like, and by combinations thereof. The coating may also be used in some embodiments to attach or to supplement the attachment of the distal stability element 140 to the filars of the drive shaft 136. Alternatively, the distal stability element 140 can be integrally formed as a unitary structure with the filars of the drive shaft 136 (e.g., using filars of a different size or density, using filars that are double-wound to provide multiple filar layers, or the like). The maximum outer diameter of the distal stability element 140 may be smaller than the maximum outer diameters of the one or more abrasive elements 138.

In some embodiments, the distal stability element 140 has an abrasive coating on its exterior surface. For example, in some embodiments a diamond coating (or other suitable type of abrasive coating) is disposed on the outer surface of the distal stability element 140. In some cases, such an abrasive surface on the distal stability element 140 can help facilitate the passage of the distal stability element 140 through vessel restrictions (such as calcified areas of a blood vessel).

In some embodiments, the distal stability element 140 has an exterior cylindrical surface that is smoother and different from an abrasive exterior surface of the one or more abrasive elements 138. That may be the case whether or not the distal stability element 140 have an abrasive coating on its exterior surface. In some embodiments, the abrasive coating on the exterior surface of the distal stability element 140 is rougher than the abrasive surfaces on the one or more abrasive elements 138.

Still referring to FIG. 1, the one or more abrasive elements 138 (which may also be referred to as a burr, multiple burrs, or (optionally) a helical array of burrs) can comprise a biocompatible material that is coated with an abrasive media such as diamond grit, diamond particles, silicon carbide, and the like. In the depicted embodiment, the abrasive elements 138 includes a total of five discrete abrasive elements that are spaced apart from each other. In some embodiments, one, two, three, four, five, six, seven, eight, nine, ten, eleven, twelve, thirteen, fourteen, fifteen, or more than fifteen discrete abrasive elements are included as the one or more abrasive elements 138. Each of the five discrete abrasive elements can include the abrasive media coating, such as a diamond grit coating.

In the depicted embodiment, the two outermost abrasive elements are smaller in maximum diameter than the three inner abrasive elements. In some embodiments, all of the abrasive elements are the same size. In particular embodiments, three or more different sizes of abrasive elements are included. Any and all such possible arrangements of sizes of abrasive elements are envisioned and within the scope of this disclosure.

Also, in the depicted embodiment, the center of mass of each abrasive element 138 is offset from the longitudinal axis of the drive shaft 136. Therefore, as the eccentric one or more abrasive elements 138 are rotated (along an orbital path), at least a portion of the abrasive surface of the one or more abrasive elements 138 can make contact with surrounding stenotic lesion material. As with the distal stability element 140, the eccentric one or more abrasive elements 138 may be mounted to the filars of the torque-transmitting coil of the drive shaft 136 using a biocompatible adhesive, high temperature solder, welding, press fitting, and the like. In some embodiments, a hypotube is crimped onto the driveshaft and an abrasive element is laser welded to the hypotube. Alternatively, the one or more abrasive elements 138 can be integrally formed as a unitary structure with the filars of the drive shaft 136 (e.g., using filars that are wound in a different pattern to create an axially offset structure, or the like).

In some embodiments, the spacing of the distal stability element 140 relative to the one or more abrasive elements 138 and the length of the distal extension portion 142 can be selected to advantageously provide a stable and predictable rotary motion profile during high-speed rotation of the drive shaft 136. For example, in embodiments that include the distal driveshaft extension portion 142, the ratio of the length of the distal driveshaft extension 142 to the distance between the centers of the one or more abrasive elements 138 and the distal stability element 140 is about 1:0.5, about 1:0.8, about 1:1, about 1.1:1, about 1.2:1, about 1.5:1, about 2:1, about 2.5:1, about 3:1, or higher than 3:1.

Still referring to FIG. 1, the rotational atherectomy system 100 also includes the actuator handle assembly 110. The actuator handle assembly 110 includes a housing 112 and a carriage assembly 114. The carriage assembly 114 is slidably translatable along the longitudinal axis of the handle assembly 110 as indicated by the arrow 115. For example, in some embodiments the carriage assembly 114 can be translated, without limitation, about 8 cm to about 12 cm, or about 6 cm to about 10 cm, or about 4 cm to about 8 cm, or about 6 cm to about 14 cm. As the carriage assembly 114 is translated in relation to the housing 112, the drive shaft 136 translates in relation to the sheath 132 in a corresponding manner.

In the depicted embodiment, the carriage assembly 114 includes a valve actuator 116. In some embodiments, an electric motor for driving rotations of the drive shaft 136 is coupled to the carriage assembly 114 such that the valve actuator 116 is an electrical switch instead. In the depicted embodiment, the valve actuator 116 is a button that can be depressed to actuate a compressed gas control valve (on/off; defaulting to off) mounted to the carriage assembly 114. While the valve actuator 116 is depressed, a compressed gas (e.g., air, nitrogen, etc.) is supplied through the valve to a turbine member that is rotatably coupled to the carriage assembly 114 and fixedly coupled to the drive shaft 136. Hence, an activation of the valve actuator 116 will result in a rotation of the turbine member and, in turn, the drive shaft 136 (as depicted by arrow 137). It should be understood that the rotational atherectomy system 100 is configured to rotate the drive shaft 136 at a high speed of rotation (e.g., 20,000-160,000 rpm) such that the eccentric one or more abrasive elements 138 revolve in an orbital path to thereby contact and remove portions of a target lesion (even those portions of the lesion that are spaced farther from the axis of the drive shaft 136 than the maximum radius of the one or more abrasive elements 138).

To operate the handle assembly 110 during a rotational atherectomy procedure, a clinician can grasp the carriage assembly 114 and depress the valve actuator 116 with the same hand. The clinician can move (translate) the carriage assembly 114 distally and proximally by hand (e.g., back and forth in relation to the housing 112), while maintaining the valve actuator 116 in the depressed state. In that manner, a target lesion(s) can be ablated radially and longitudinally by virtue of the resulting orbital rotation and translation of the one or more abrasive elements 138, respectively.

During an atherectomy treatment, in some cases the guidewire 134 is left in position in relation to the drive shaft 136 generally as shown. For example, in some cases the portion of the guidewire 134 that is extending beyond the distal end of the drive shaft 136 (or extension portion 142) is about 10 inches to about 12 inches (about 25 cm to about 30 cm), about 6 inches to about 16 inches (about 15 cm to about 40 cm), or about 2 inches to about 20 inches (about 5 cm to about 50 cm). In some cases, the guidewire 134 is pulled back to be within (while not extending distally from) the drive shaft 136 during an atherectomy treatment. The distal end of the guidewire 134 may be positioned anywhere within the drive shaft 136 during an atherectomy treatment. In some cases, the guidewire 134 may be completely removed from within the drive shaft during an atherectomy treatment. The extent to which the guidewire 134 is engaged with the drive shaft 136 during an atherectomy treatment may affect the size of the orbital path of the one or more abrasive elements 138. Accordingly, the extent to which the guidewire 134 is engaged with the drive shaft 136 may be situationally selected to be well-suited for a particular patient anatomy, physician's preference, type of treatment being delivered, and other such factors.

In the depicted embodiment, the handle assembly 110 also includes a guidewire detention mechanism 118. The guidewire detention mechanism 118 can be selectively actuated (e.g., rotated) to releasably clamp and maintain the guidewire 134 in a stationary position relative to the handle assembly 110 (and, in turn, stationary in relation to rotations of the drive shaft 136 during an atherectomy treatment). While the drive shaft 136 and handle assembly 110 are being advanced over the guidewire 134 to put the one or more abrasive elements 138 into a targeted position within a patient's vessel, the guidewire detention mechanism 118 will be unactuated so that the handle assembly 110 is free to slide in relation to the guidewire 134. Then, when the clinician is ready to begin the atherectomy treatment, the guidewire detention mechanism 118 can be actuated to releasably detain/lock the guidewire 134 in relation to the handle assembly 110. That way the guidewire 134 will not rotate while the drive shaft 136 is rotating, and the guidewire 134 will not translate while the carriage assembly 114 is being manually translated.

Still referring to FIG. 1, the rotational atherectomy system 100 also includes the controller 150. In the depicted embodiment, the controller 150 includes a user interface 152 that includes a plurality of selectable inputs 154 that correspond to a plurality of rotational speeds or, in some embodiments, vessel sizes (diameters). To operate the rotational atherectomy system 100, the user can select a particular one of the selectable inputs 154 in accordance with the desired rotational speed or vessel size. In response, the controller 150 will determine the appropriate gas pressure for rotating the drive shaft 136 at the selected rotational speed or in a vessel of the selected diameter (faster rpm for larger vessels and slower rpm for smaller vessel), and supply the gas at the appropriate pressure to the handle assembly 110.

In some embodiments, the controller 150 is pole-mounted. The controller 150 can be used to control particular operations of the handle assembly 110 and the drive shaft assembly 130. For example, the controller 150 can be used to compute, display, and adjust the rotational speed of the drive shaft 136.

In some embodiments, the controller 150 can include electronic controls that are in electrical communication with a turbine RPM sensor located on the carriage assembly 114. The controller 150 can convert the signal(s) from the sensor into a corresponding RPM quantity and display the RPM on the user interface 152. If a speed adjustment is desired, the clinician can increase or decrease the rotational speed of the drive shaft 136. In result, a flow or pressure of compressed gas supplied from the controller 150 to the handle assembly 110 (via the cable assembly 160) will be modulated. The modulation of the flow or pressure of the compressed gas will result in a corresponding modulation of the RPM of the turbine member and of the drive shaft 136.

In some embodiments, the controller 150 includes one or more interlock features that can enhance the functionality of the rotational atherectomy system 100. In one such example, if the controller 150 does not detect any electrical signal (or a proper signal) from the turbine RPM sensor, the controller 150 can discontinue the supply of compressed gas. In another example, if a pressure of a flush liquid supplied to the sheath 132 is below a threshold pressure value, the controller 150 can discontinue the supply of compressed gas.

Referring to FIG. 2, a distal end portion of the drive shaft 136 is shown in a longitudinal cross-sectional view. The distal end portion of the drive shaft 136 includes the one or more abrasive elements 138 that are eccentrically-fixed to the driveshaft 136, the optional distal stability element 140 with an abrasive outer surface, and the distal drive shaft extension portion 142.

In the depicted embodiment, the one or more abrasive elements 138 includes a total of five discrete abrasive elements that are spaced apart from each other. In some embodiments, one, two, three, four, five, six, seven, eight, nine, ten, eleven, twelve, thirteen, fourteen, fifteen, or more than fifteen discrete abrasive elements are included as the one or more abrasive elements 138. Each of the five discrete abrasive elements can include the abrasive media coating.

In the depicted embodiment, the two outermost abrasive elements of the abrasive elements 138 are smaller in maximum diameter than the three inner abrasive elements of the abrasive elements 138. In some embodiments, all of the abrasive elements are the same size. In particular embodiments, three or more different sizes of abrasive elements are included. Any and all such possible arrangements of sizes of abrasive elements are envisioned and within the scope of this disclosure.

The one or more abrasive elements 138 can be made to any suitable size. For clarity, the size of the one or more abrasive elements 138 will refer herein to the maximum outer diameter of individual abrasive elements of the one or more abrasive elements 138. In some embodiments, the one or more abrasive elements 138 are about 2 mm in size (maximum outer diameter). In some embodiments, the size of the one or more abrasive elements 138 is in a range of about 1.5 mm to about 2.5 mm, or about 1.0 mm to about 3.0 mm, or about 0.5 mm to about 4.0 mm, without limitation. Again, in a single embodiment, one or more of the abrasive elements 138 can have a different size in comparison to the other abrasive elements 138. In some embodiments, the two outermost abrasive elements are about 1.5 mm in diameter and the inner abrasive elements are about 2.0 mm in diameter.

In the depicted embodiment, the one or more abrasive elements 138, individually, are oblong in shape. A variety of different shapes can be used for the one or more abrasive elements 138. For example, in some embodiments the one or more abrasive elements 138 are individually shaped as spheres, discs, rods, cylinders, polyhedrons, cubes, prisms, and the like. In some embodiments, such as the depicted embodiment, all of the one or more abrasive elements 138 are the same shape. In particular embodiments, one or more of the abrasive elements 138 has a different shape than one or more of the other abrasive elements 138. That is, two, three, or more differing shapes of individual abrasive elements 138 can be combined on the same drive shaft 136.

In the depicted embodiment, adjacent abrasive elements of the one or more abrasive elements 138 are spaced apart from each other. For example, in the depicted embodiment the two distal-most individual abrasive elements are spaced apart from each other by a distance 'X'. In some embodiments, the spacing between adjacent abrasive elements is consistent between all of the one or more abrasive elements 138. Alternatively, in some embodiments the spacing between some adjacent pairs of abrasive elements differs from the spacing between other adjacent pairs of abrasive elements.

In some embodiments, the spacing distance X in ratio to the maximum diameter of the abrasive elements 138 is about 1:1. That is, the spacing distance X is about equal to the maximum diameter. The spacing distance X can be selected to provide a desired degree of flexibility of the portion of the drive shaft 136 to which the one or more abrasive elements 138 are attached. In some embodiments, the ratio is about 1.5:1 (i.e., X is about 1.5 times longer than the maximum diameter). In some embodiments, the ratio is in a range of about 0.2:1 to about 0.4:1, or about 0.4:1 to about 0.6:1, or about 0.6:1 to about 0.8:1, or about 0.8:1 to about 1:1, or about 1:1 to about 1.2:1, or about 1.2:1 to about 1.4:1, or about 1.4:1 to about 1.6:1, or about 1.6:1 to about 1.8:1, or about 1.8:1 to about 2.0:1, or about 2.0:1 to about 2.2:1, or about 2.2:1 to about 2.4:1, or about 2.4:1 to about 3.0:1, or about 3.0:1 to about 4.0:1, and anywhere between or beyond those ranges.

In the depicted embodiment, the center of mass of each one of the one or more abrasive elements 138 is offset from the longitudinal axis of the drive shaft 136 along a same radial angle. Said another way, the centers of mass of all of the one or more abrasive elements 138 are coplanar with the longitudinal axis of the drive shaft 136. If the size of each of the one or more abrasive elements 138 is equal, the centers of mass of the one or more abrasive elements 138 would be collinear on a line that is parallel to the longitudinal axis of the drive shaft 136.

Referring to FIG. 3, according to some embodiments of the rotational atherectomy devices provided herein, one or more abrasive elements 144 are arranged at differing radial angles in relation to the drive shaft 136 as depicted here. In such a case, a path defined by the centers of mass of the one or more abrasive elements 144 spirals along the drive shaft 136 around the central longitudinal axis of the drive shaft 136. In some cases (e.g., when the diameters of the one or more abrasive elements 144 are equal and the adjacent abrasive elements are all equally spaced), the centers of mass of the one or more abrasive elements 144 define a helical path along/around the drive shaft 136. It has been found that such arrangements can provide a desirably-shaped orbital rotation of the one or more abrasive elements 144.

It should be understood that any of the structural features described in the context of one embodiment of the rotational atherectomy devices provided herein can be combined with any of the structural features described in the context of one or more other embodiments of the rotational atherectomy devices provided herein. For example, the size, spacing, and/or shape features (and any other characteristics) of the one or more abrasive elements 138 described in the context of FIGS. 1 and 2 can be incorporated in any desired combination with the spiral arrangement of the one or more abrasive elements 144.

In some embodiments, the drive shaft assembly 130 includes at least four abrasive elements 144 attached to a distal end portion of the drive shaft 136 and each has a center of mass offset from the longitudinal axis of the drive shaft 136. A spiral path defined by connecting the centers of mass of the at least four abrasive elements 144 spirals around the longitudinal axis of the drive shaft 136. An overall radial angle of the spiral path is defined by a radial angle between a distal-most abrasive element of the at least four abrasive elements 144 and a proximal-most abrasive element of the at least four abrasive elements 144. In some embodiments, the overall radial angle of the spiral path of the at least four abrasive elements 144 is always less than 180 degrees along any 10 cm length of the distal end portion of the drive shaft 136. In some embodiments, the overall radial angle of the spiral path of the at least four abrasive elements 144 is always less than 170 degrees, or less than 160 degrees, or less than 150 degrees, or less than 140 degrees, or less than 130 degrees, or less than 120 degrees, or less than 110 degrees, or less than 100 degrees, or less than 90 degrees along any 10 cm length of the distal end portion of the drive shaft 136.

In some embodiments, such as the depicted embodiment, the drive shaft assembly 130 includes a concentric abrasive tip member 141. The concentric abrasive tip member 141 can be affixed to, and extending distally from, a distal-most end of the drive shaft 136. In some embodiments that include the concentric abrasive tip member 141, no distal stability element is included 140. In particular embodiments (such as the depicted embodiment), the concentric abrasive tip member 141 and the distal stability element are both included 140.

In some embodiments the concentric abrasive tip member 141 may be made of metallic materials such as stainless steel, tungsten, molybdenum, iridium, cobalt, cadmium, and the like, and alloys thereof. The concentric abrasive tip member 141 has a fixed outer diameter. That is, the concentric abrasive tip member 141 is not an expandable member in the depicted embodiment. The concentric abrasive tip member 141 may be mounted to the filars of the drive shaft 136 using a biocompatible adhesive, by welding, by press fitting, and the like, and by combinations thereof. Alternatively, the concentric abrasive tip member 141 can be integrally formed as a unitary structure with the filars of the drive shaft 136 (e.g., using filars of a different size or density, using filars that are double-wound to provide multiple filar layers, or the like).

In some embodiments, the concentric abrasive tip member 141 has an abrasive coating on its exterior surface. In particular embodiments, the concentric abrasive tip member 141 includes an abrasive material along an exterior circumferential surface, or on a distal end face/surface, or both. For example, in some embodiments a diamond coating (or other suitable type of abrasive coating) is disposed on the outer surface of the concentric abrasive tip member 141. In some cases, such an abrasive surface on the concentric abrasive tip member 141 can help facilitate the passage of the concentric abrasive tip member 141 through vessel restrictions (such as calcified areas of a blood vessel).

In some embodiments, the concentric abrasive tip member 141 has an exterior surface that is smoother and different from an abrasive exterior surface of the one or more abrasive elements 138. That may be the case whether or not the concentric abrasive tip member 141 have an abrasive coating on its exterior surface. In some embodiments, the abrasive coating on the exterior surface of the concentric abrasive tip member 141 is rougher than the abrasive surfaces on the one or more abrasive elements 138.

The maximum outer diameter of the concentric abrasive tip member 141 may be smaller than, equal to, or larger than the outer diameter of the adjacent portion of the drive shaft 136. The maximum outer diameter of the concentric abrasive tip member 141 may be smaller than, equal to, or larger than the maximum outer diameter of each of the one or more abrasive elements 144a-e. The lateral width of the concentric abrasive tip member 141 (e.g., measured parallel to the longitudinal axis of the drive shaft 136) may be smaller than, equal to, or larger than the maximum lateral width of each of the one or more abrasive elements 144a-e.

The concentric abrasive tip member 141 defines a central opening that is coaxial with the lumen defined by the drive shaft 136. Accordingly, a guidewire (e.g., the guidewire 134 of FIG. 1) can extend through the concentric abrasive tip member 141. In some embodiments, the concentric abrasive tip member 141 is shaped as a toroid. In particular embodiments, the concentric abrasive tip member 141 is shaped as a hollow cylinder. In certain embodiments, the outer surface of the concentric abrasive tip member 141 defines one or more grooves, teeth, edges, and the like, and combinations thereof.

Referring also to FIGS. 4-8, the differing radial angles of the individual abrasive elements 144a, 144b, 144c, 144d, and 144e can be further visualized. To avoid confusion, each figure of FIGS. 4-8 illustrates only the closest one of the individual abrasive elements 144a, 144b, 144c, 144d, and 144e (i.e., closest in terms of the corresponding cutting-plane as shown in FIG. 3). For example, in FIG. 5, abrasive element 144b is shown, but abrasive element 144a is not shown (so that the radial orientation of the abrasive element 144b is clearly depicted).

It can be seen in FIGS. 4-8 that the centers of mass of abrasive elements 144a, 144b, 144c, 144d, and 144e are at differing radial angles in relation to the drive shaft 136. Hence, it can be said that the abrasive elements 144a, 144b, 144c, 144d, and 144e are disposed at differing radial angles in relation to the drive shaft 136.

In the depicted embodiment, the radial angles of the abrasive elements 144a, 144b, 144c, 144d, and 144e differ from each other by a consistent 37.5 degrees (approximately) in comparison to the adjacent abrasive element(s). For example, the center of mass of abrasive element 144b is disposed at a radial angle B that is about 37.5 degrees different than the angle at which the center of mass of abrasive element 144a is disposed, and about 37.5 degrees different than the angle C at which the center of mass of abrasive element 144c is disposed. Similarly, the center of mass of abrasive element 144c is disposed at a radial angle C that is about 37.5 degrees different than the angle B at which the center of mass of abrasive element 144b is disposed, and about 37.5 degrees different than the angle D at which the center of mass of abrasive element 144d is disposed. The same type of relative relationships can be said about abrasive element 144d.

While the depicted embodiment has a relative radial offset of 37.5 degrees (approximately) in comparison to the adjacent abrasive element(s), a variety of other relative radial offsets are envisioned. For example, in some embodiments the relative radial offsets of the adjacent abrasive elements is in a range of about 0 degrees to about 5 degrees, or about 5 degrees to about 10 degrees, or about 10 degrees to about 15 degrees, or about 15 degrees to about 20 degrees, or about 20 degrees to about 25 degrees, or about 25 degrees to about 30 degrees, or about 30 degrees to about 35 degrees, or about 10 degrees to about 30 degrees, or about 20 degrees to about 40 degrees, or about 20 degrees to about 50 degrees.

While in the depicted embodiment, the relative radial offsets of the abrasive elements 144a, 144b, 144c, 144d, and 144e in comparison to the adjacent abrasive element(s) are consistent, in some embodiments some abrasive elements are radially offset to a greater or lesser extent than others. For example, while angles B, C, D, and E are all multiples of 37.5 degrees, in some embodiments one or more of the angles B, C, D, and/or E is not a multiple of the same angle as the others.

The direction of the spiral defined by the centers of mass of the abrasive elements 144a, 144b, 144c, 144d, and 144e can be in either direction around the drive shaft 136, and in either the same direction as the wind of the filars or in the opposing direction as the wind of the filars.

Figure 9:
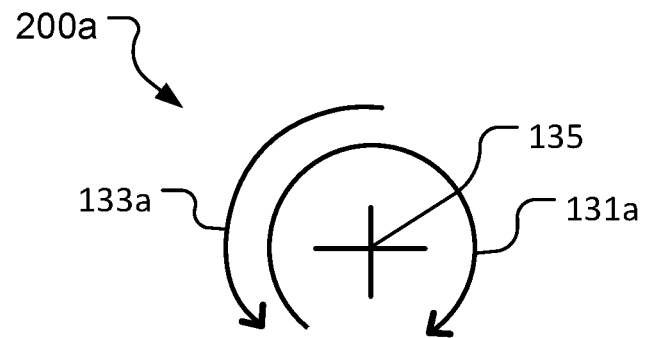
FIG. 9 is a schematic diagram representing an example drive shaft embodiment that includes filars that are wound in a direction opposite to the direction of a spiral path defined by multiple abrasive elements that are arranged at differing radial angles.

Referring also to FIG. 9, a schematic diagram 200a depicting an end view of the drive shaft 136 (looking distally) with the abrasive elements 144a-e can be used to illustrate the filar spiral wind direction 131a (of the drive shaft 136) in comparison to the spiral path defined by the abrasive element centers of mass 133a (of the abrasive elements 144a-e). In the depicted embodiment, the filar spiral wind direction 131a is clockwise around the central longitudinal axis 135 of the drive shaft 136. In contrast, the spiral path defined by the abrasive element centers of mass 133a is counterclockwise around the central longitudinal axis 135 of the drive shaft 136. In other words, the filar spiral wind direction 131a and the spiral path defined by the abrasive element centers of mass 133a are opposite of each other.

Figure 10:
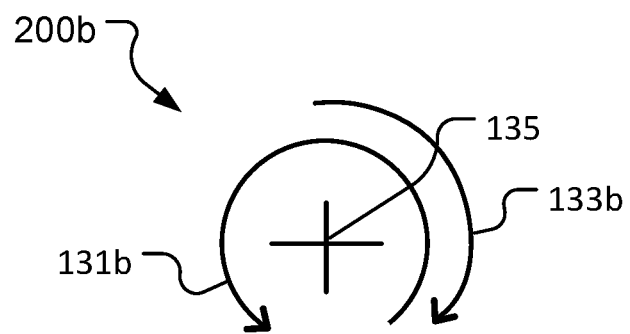
FIG. 10 is a schematic diagram representing another example drive shaft embodiment that includes filars that are wound in a direction opposite to the direction of a spiral path defined by multiple abrasive elements that are arranged at differing radial angles.

Referring also to FIG. 10, another schematic diagram 200b depicting an end view of the drive shaft 136 (looking distally) with the abrasive elements 144a-e can be used to illustrate another arrangement of the filar spiral wind direction 131b (of the drive shaft 136) in comparison to the spiral path defined by the abrasive element centers of mass 133b (of the abrasive elements 144a-e). In this depicted embodiment, the filar spiral wind direction 131b is counterclockwise around the central longitudinal axis 135 of the drive shaft 136. In contrast, the spiral path defined by the abrasive element centers of mass 133b is clockwise around the central longitudinal axis 135 of the drive shaft 136. In other words, the filar spiral wind direction 131b and the spiral path defined by the abrasive element centers of mass 133b are opposite of each other.

The relationship between filar spiral wind direction (e.g., of the drive shaft 136) in comparison to the spiral path defined by the abrasive element centers of mass (e.g., of the abrasive elements 144a-e) will be described further below in reference to FIGS. 18 and 19.

Figure 11:
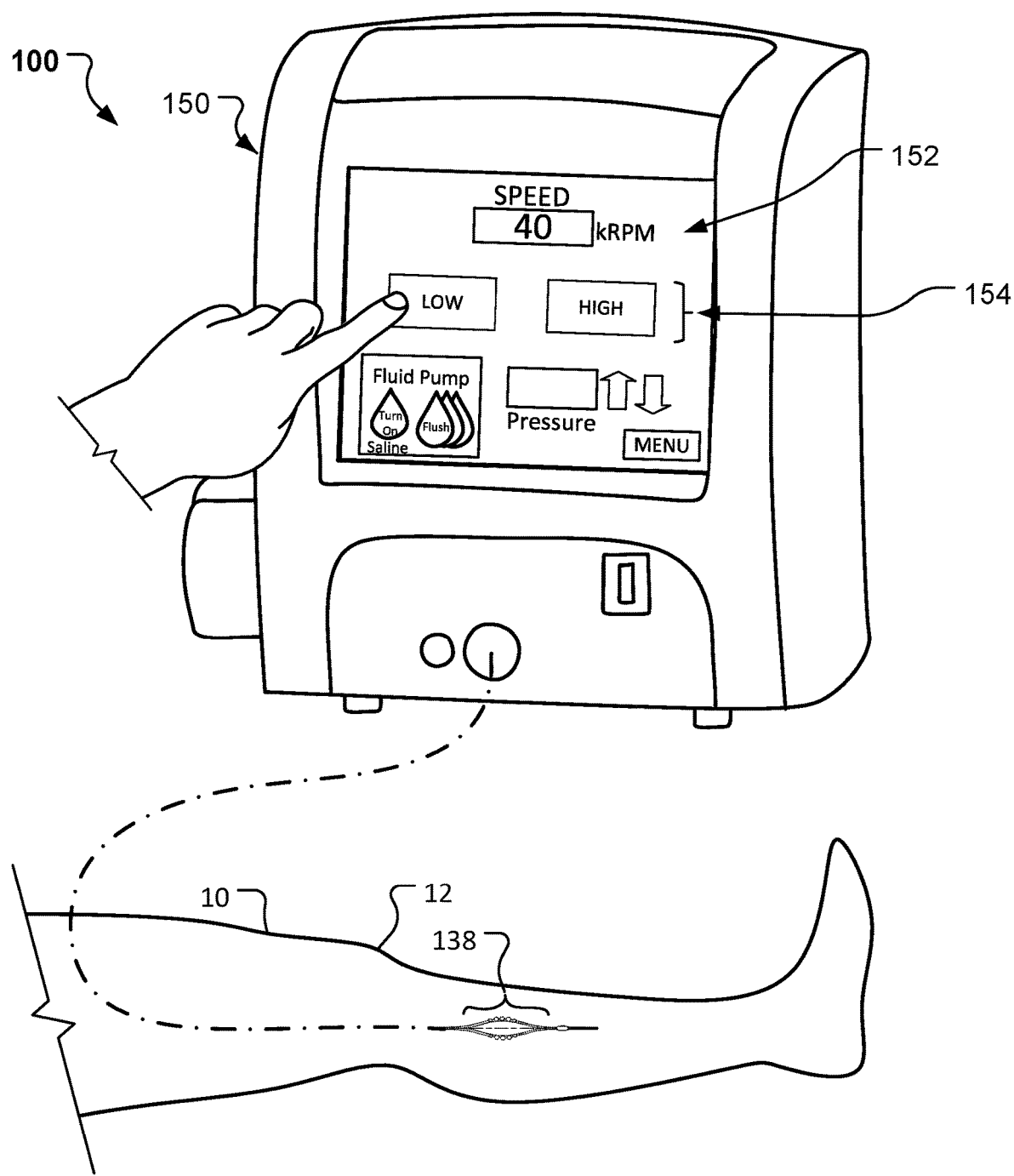
FIG. 11 shows an example implementation of a rotational atherectomy system that is being operated by a clinician-user to perform a rotational atherectomy procedure below the knee of a patient.

Referring to FIG. 11, the rotational atherectomy system 100 can be used to treat, for example, a leg 10 of a patient. In the depicted embodiment of rotational atherectomy system 100, the controller 150 includes a user interface 152 that includes a plurality of selectable inputs 154 that correspond to a plurality of rotational speeds or, in some embodiments, vessel sizes (diameters). To operate the rotational atherectomy system 100, the user can select a particular one of the selectable inputs 154 in accordance with the desired rotational speed or vessel size. In response, the controller 150 will determine the appropriate gas pressure for rotating the drive shaft 136 at the selected rotational speed or in a vessel of the selected diameter (faster rpm for larger vessels and slower rpm for smaller vessel), and supply the gas at the appropriate pressure to the handle assembly 110. In some embodiments, the driver for rotation of the one or more abrasive elements 138 is an electrical motor rather than the pneumatic motor included in the depicted example.

In the depicted example, the vessel to be treated is in the leg 10 of a patient. In particular, the vessel is below a knee 12 (e.g., a tibial artery, without limitation). Such a vessel can tend to be relatively small in diameter. Therefore, in this illustrative example, the clinician user is inputting a vessel size of 4.0 mm. In response, the controller 150 will determine the appropriate gas pressure for rotating the one or more abrasive elements 138 in a 4.0 mm vessel. For example, that speed may be about 40,000 rpm. The corresponding gas pressure will be supplied to the handle assembly 110 via cable assembly 160 (FIG. 1).

Figure 12:
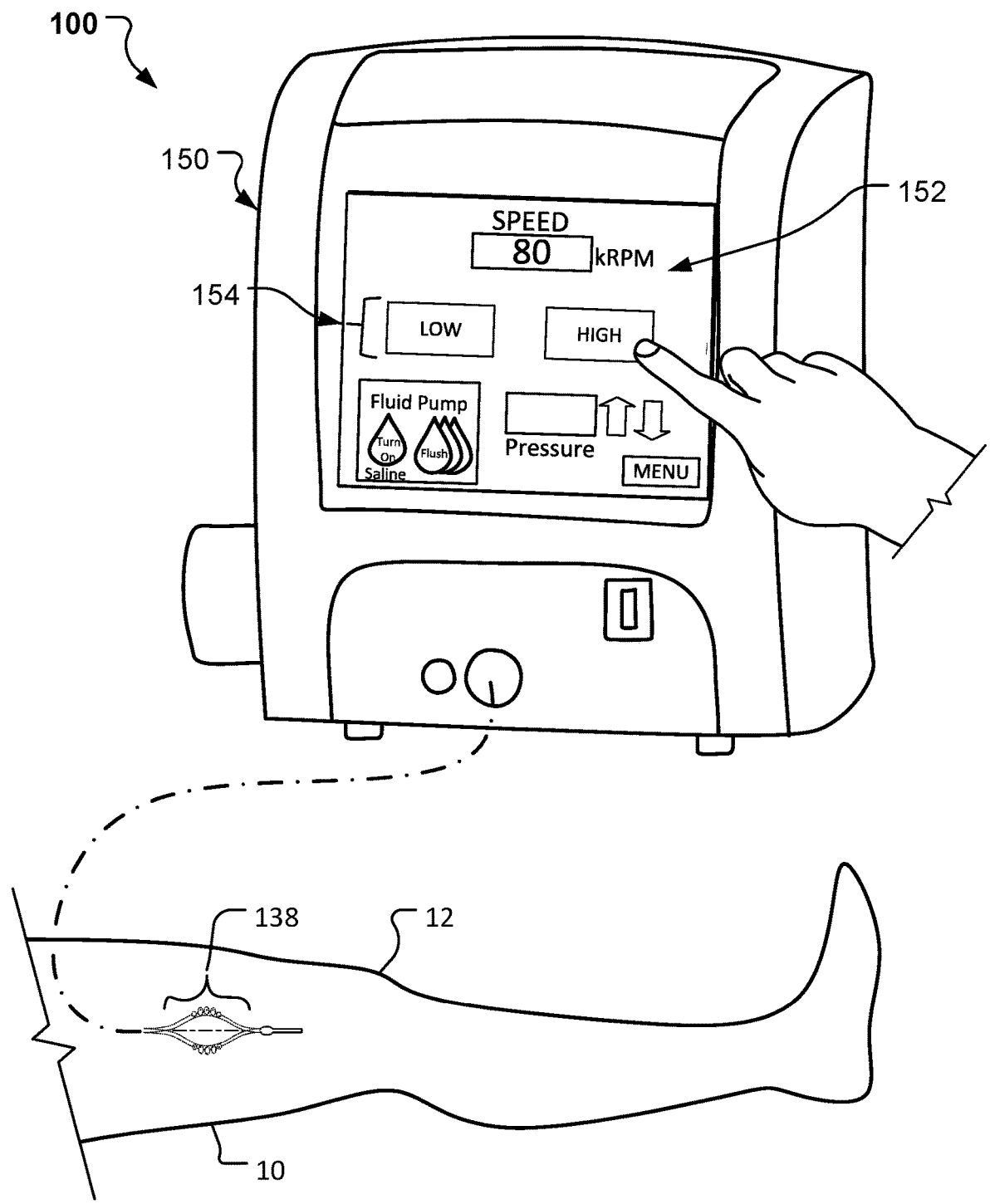
FIG. 12 shows the example implementation of FIG. 11 being operated to perform a rotational atherectomy procedure above the knee of a patient.
Figure 13:
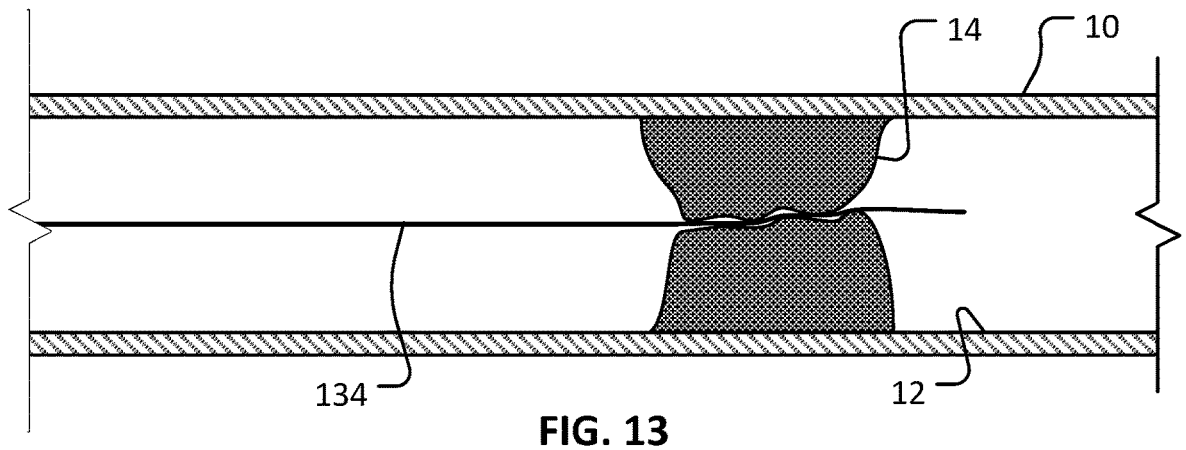
FIG. 13 shows a guidewire being advanced through a lesion in a blood vessel.

Referring to FIG. 12, in another example, the vessel to be treated is above the knee 12. For example, without limitation, the vessel may be an iliac or femoral artery. Such a vessel will tend to be relatively large in diameter. Therefore, in this illustrative example, the clinician user is inputting a vessel size of 8.0 mm. In response, the controller 150 will determine the appropriate gas pressure for rotating the one or more abrasive elements 138 in an 8.0 mm vessel. For example, that speed may be about 80,000 rpm. The corresponding gas pressure will be supplied to the handle assembly 110 via cable assembly 160 (FIG. 1).

Referring also to FIGS. 13-17, the rotational atherectomy system 100 can be used to treat a vessel 10 having a stenotic lesion 14 along an inner wall 12 of the vessel 10. The rotational atherectomy system 100 is used to fully or partially remove the stenotic lesion 14, thereby removing or reducing the blockage within the vessel 10 caused by the stenotic lesion 14. By performing such a treatment, the blood flow through the vessel 10 may be thereafter increased or otherwise improved. The vessel 10 and lesion 14 are shown in longitudinal cross-sectional views to enable visualization of the rotational atherectomy system 100.

Briefly, in some implementations the following activities may occur to achieve the deployed arrangement shown in FIGS. 13-17. In some embodiments, an introducer sheath (not shown) can be percutaneously advanced into the vasculature of the patient. The guidewire 134 can then be inserted through a lumen of the introducer sheath and navigated within the patient's vasculature to a target location (e.g., the location of the lesion 14). Techniques such as x-ray fluoroscopy or ultrasonic imaging may be used to provide visualization of the guidewire 134 and other atherectomy system components during placement. In some embodiments, no introducer sheath is used and the guidewire 134 is inserted without assistance from a sheath. The resulting arrangement is depicted in FIG. 2.

Figure 14:
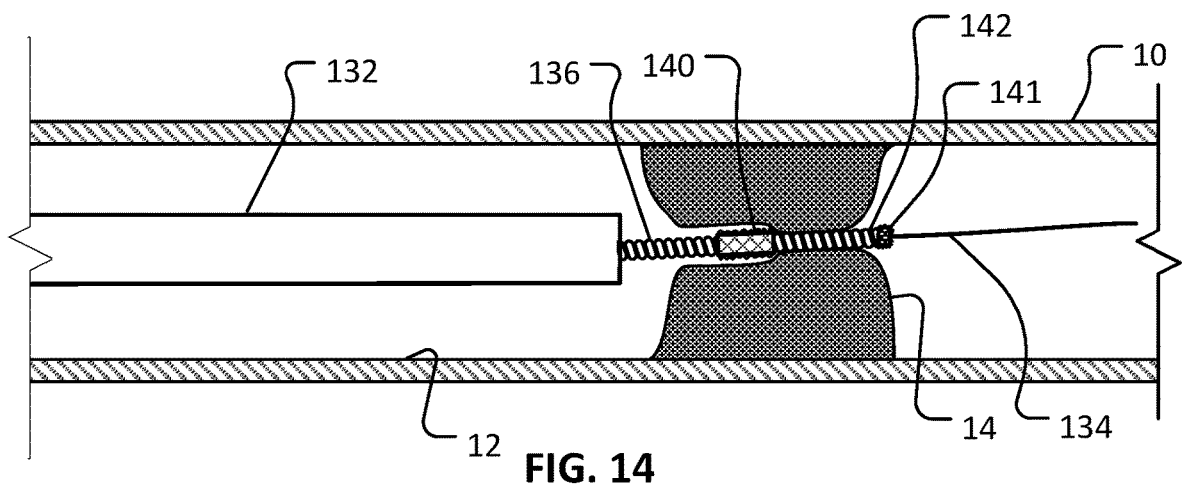
FIG. 14 shows an example rotational atherectomy device being advanced over the guidewire of FIG. 13 and into region of the lesion.

Next, as depicted in FIG. 14, portions of the rotational atherectomy system 100 can be inserted over the guidewire 134. For example, an opening to the lumen of the drive shaft 136 at the distal free end of the drive shaft 136 (e.g., at the distal end of the optional distal drive shaft extension portion 142) and/or an opening to the lumen of the drive shaft 136 via the optional concentric abrasive tip member 141 (as shown) can be placed onto the guidewire 134, and then the drive shaft assembly 130 and handle assembly 110 can be gradually advanced over the guidewire 134 to the position in relation to the lesion 14 as shown. In some cases, the drive shaft 136 is disposed fully within the lumen of the sheath 132 during the advancing. In some cases, a distal end portion of the drive shaft 136 extends from the distal end opening 143 of the sheath 132 during the advancing. Eventually, after enough advancing, the proximal end of the guidewire 134 will extend proximally from the handle assembly 110 (via the access port 120 defined by the handle housing 112).

In some cases (such as in the depicted example), the lesion 14 may be so large (i.e., so extensively occluding the vessel 10) that it is difficult or impossible to push the drive shaft 136 into and/or through the lesion 14. In some such cases, an abrasive outer surface on the concentric abrasive tip member 141 and/or distal stability element 140 can be used to help facilitate passage of the distal end portion of the drive shaft 136 into or through the lesion 14. In some such cases, the drive shaft 136 can be rotated to further help facilitate the concentric abrasive tip member 141 and/or distal stability element 140 to bore into/through the lesion 14.

Figure 15:
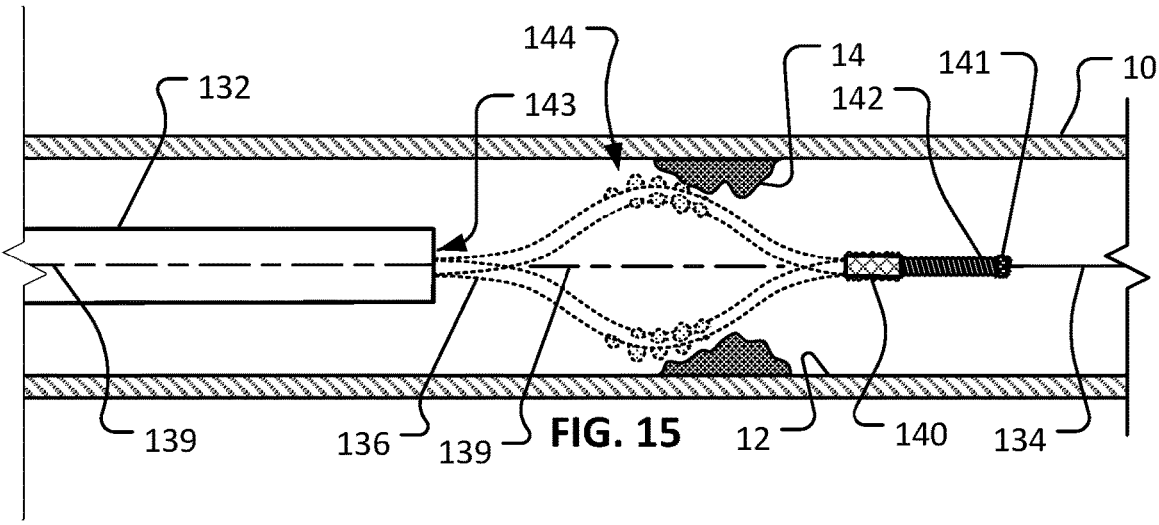
FIG. 15 shows the example rotational atherectomy device of FIG. 14 in use at a first longitudinal position in the region of the lesion. A multi-portion abrasive element of the rotational atherectomy device is being rotated along an orbital path to abrade the lesion.
Figure 16:
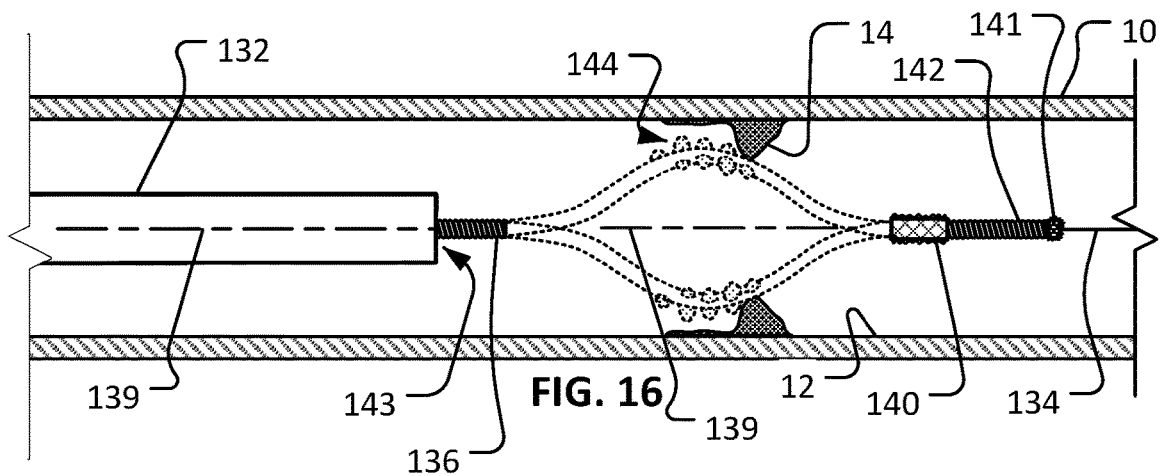
FIG. 16 shows the rotational atherectomy device of FIG. 14 with the abrasive element being rotated at a second longitudinal position that is distal of the first longitudinal position.
Figure 17:
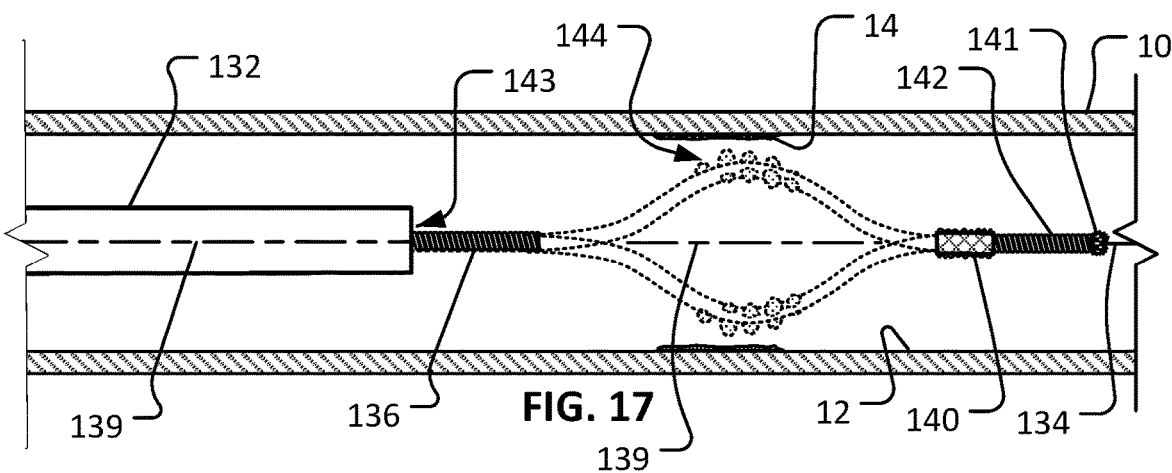
FIG. 17 shows the rotational atherectomy device of FIG. 14 with the abrasive element being rotated at a third longitudinal position that is distal of the second longitudinal position.

Next, as depicted by FIGS. 15-17, the rotation and translational motions of the drive shaft 136 (and the one or more abrasive elements 144) can be commenced to perform ablation of the lesion 14.

In some implementations, prior to the ablation of the lesion 14 by the one or more abrasive elements 144, an inflatable member can be used as an angioplasty balloon to treat the lesion 14. That is, an inflatable member (on the sheath 132, for example) can be positioned within the lesion 14 and then inflated to compress the lesion 14 against the inner wall 12 of the vessel 10. Thereafter, the rotational atherectomy procedure can be performed. In some implementations, such an inflatable member can be used as an angioplasty balloon after the rotational atherectomy procedure is performed. In some implementations, additionally or alternatively, a stent can be placed at lesion 14 using an inflatable member on the sheath 132 (or another balloon member associated with the drive shaft assembly 130) after the rotational atherectomy procedure is performed.

The guidewire 134 may remain extending from the distal end of the drive shaft 136 during the atherectomy procedure as shown. For example, as depicted by FIGS. 15-17, the guidewire 134 extends through the lumen of the drive shaft 136 and further extends distally of the distal end of the distal extension portion 142 during the rotation and translational motions of the drive shaft 136 (refer, for example, to FIGS. 15-17). In some alternative implementations, the guidewire 134 is withdrawn completely out of the lumen of the drive shaft 136 prior to during the rotation and translational motions of the drive shaft 136 for abrading the lesion 14. In other implementations, the guidewire is withdrawn only partially. That is, in some implementations a portion of the guidewire remains within the lumen of the drive shaft 136 during rotation of the drive shaft 136, but remains only in a proximal portion that is not subject to the significant orbital path in the area of the one or more abrasive elements 144 (e.g., remains within the portion of the drive shaft 136 that remains in the sheath 132).

To perform the atherectomy procedure, the drive shaft 136 is rotated at a high rate of rotation (e.g., 20,000-160,000 rpm) such that the eccentric one or more abrasive elements 144 revolve in an orbital path about an axis of rotation and thereby contacts and removes portions of the lesion 14.

Still referring to FIGS. 15-17, the rotational atherectomy system 100 is depicted during the high-speed rotation of the drive shaft 136. The centrifugal force acting on the eccentrically weighted one or more abrasive elements 144 causes the one or more abrasive elements 144 to orbit in an orbital path around the axis of rotation 139. In some implementations, the orbital path can be somewhat similar to the orbital motion of a "jump rope." As shown, some portions of the drive shaft 136 (e.g., a portion that is just distal of the sheath 132 and another portion that is distal of the distal stability element 140) can remain in general alignment with the axis of rotation 139, but the particular portion of the drive shaft 136 adjacent to the one or more abrasive elements 144 is not aligned with the axis of rotation 139 (and instead orbits around the axis 139). As such, in some implementations, the axis of rotation 139 may be aligned with the longitudinal axis of a proximal part of the drive shaft 136 (e.g., a part within the distal end of the sheath 132) and with the longitudinal axis of the distal extension portion 142 of the drive shaft 136.

In some implementations, as the one or more abrasive elements 144 rotates, the clinician operator slowly advances the carriage assembly 114 distally (and, optionally, reciprocates both distally and proximally) in a longitudinal translation direction so that the abrasive surface of the one or more abrasive elements 144 scrapes against additional portions of the occluding lesion 14 to reduce the size of the occlusion, and to thereby improve the blood flow through the vessel 10. This combination of rotational and translational motion of the one or more abrasive elements 144 is depicted by the sequence of FIGS. 15-17.

In some embodiments, the sheath 132 may define one or more lumens (e.g., the same lumen as, or another lumen than, the lumen in which the drive shaft 136 is located) that can be used for aspiration (e.g., of abraded particles of the lesion 14). In some cases, such lumens can be additionally or alternatively used to deliver perfusion and/or therapeutic substances to the location of the lesion 14, or to prevent backflow of blood from vessel 10 into sheath 132.

Figure 18:
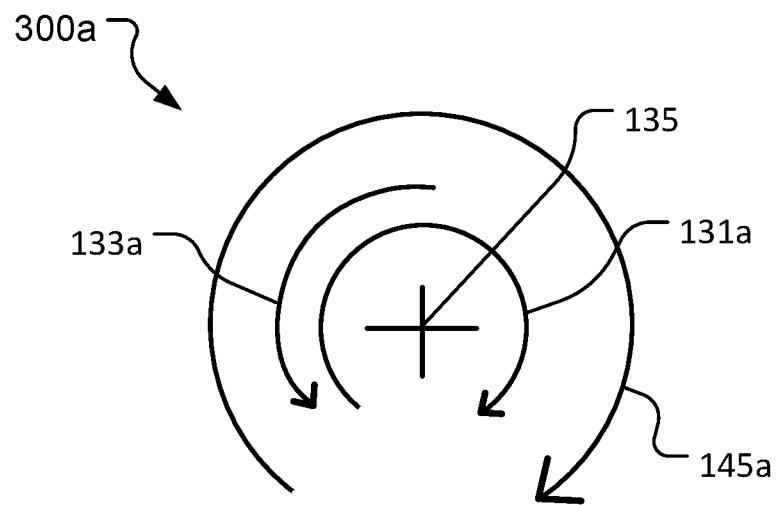
FIG. 18 is a schematic diagram representing an example drive shaft embodiment that includes filars that are wound in a direction opposite to the direction of a spiral path defined by multiple abrasive elements that are arranged at differing radial angles, and that is being rotated during use in the same direction as the filars are wound.

Referring also to FIG. 18, a schematic diagram 300*a* depicting an end view of the drive shaft 136 (looking distally) with the abrasive elements 144 can be used to illustrate the filar spiral wind direction 131*a* (of the drive shaft 136) in comparison to the spiral path defined by the abrasive element centers of mass 133*a* (of the abrasive elements 144), and also in comparison to the rotation direction 145*a* of the drive shaft 136 during use. In the depicted embodiment, the filar spiral wind direction 131*a* is clockwise around the central longitudinal axis 135 of the drive shaft 136. Also, the rotation direction 145*a* of the drive shaft 136 during use is clockwise around the central longitudinal axis 135 of the drive shaft 136. In contrast, the spiral path defined by the abrasive element centers of mass 133*a* is counterclockwise around the central longitudinal axis 135 of the drive shaft 136. In other words, the filar spiral wind direction 131*a* and the rotation direction 145*a* of the drive shaft 136 during use are the same direction, whereas the spiral path defined by the abrasive element centers of mass 133*a* is the opposite direction of: (i) the filar spiral wind direction 131*a* and (ii) the opposite direction of the rotation direction 145*a* of the drive shaft 136 during use.

Figure 19:
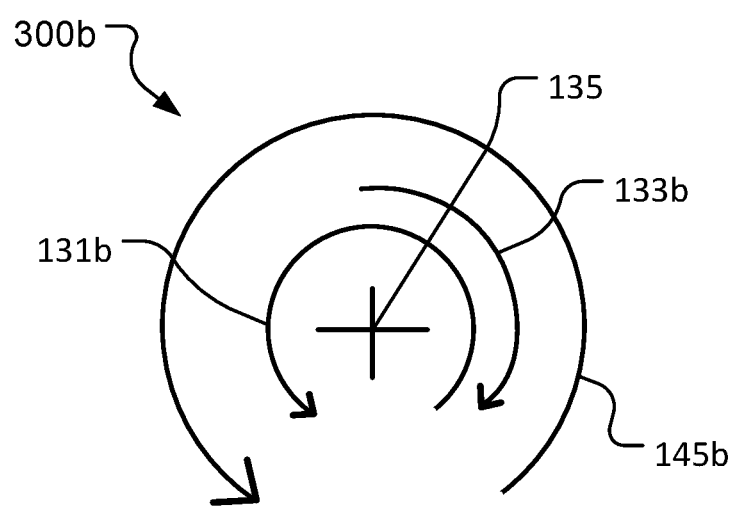
FIG. 19 is a schematic diagram representing another example drive shaft embodiment that includes filars that are wound in a direction opposite to the direction of a spiral path defined by multiple abrasive elements that are arranged at differing radial angles, and that is being rotated during use in the same direction as the filars are wound.

Referring also to FIG. 19, another schematic diagram 300*b* depicting an end view of the drive shaft 136 (looking distally) with the abrasive elements 144 can be used to illustrate the filar spiral wind direction 131*b* (of the drive shaft 136) in comparison to the spiral path defined by the abrasive element centers of mass 133*b* (of the abrasive elements 144), and also in comparison to the rotation direction 145*b* of the drive shaft 136 during use. In the depicted embodiment, the filar spiral wind direction 131*b* is counterclockwise around the central longitudinal axis 135 of the drive shaft 136. Also, the rotation direction 145*b* of the drive shaft 136 during use is counterclockwise around the central longitudinal axis 135 of the drive shaft 136. In contrast, the spiral path defined by the abrasive element centers of mass 133*b* is clockwise around the central longitudinal axis 135 of the drive shaft 136. In other words, here again in this example, the filar spiral wind direction 131*b* and the rotation direction 145*b* of the drive shaft 136 during use are the same direction, whereas the spiral path defined by the abrasive element centers of mass 133*b* is the opposite direction of: (i) the filar spiral wind direction 131*b* and (ii) the opposite direction of the rotation direction 145*b* of the drive shaft 136 during use.

The relative arrangements between: (i) the filar spiral wind direction 131*a* or 131*b*, (ii) the spiral path defined by the abrasive element centers of mass 133*a* or 133*b*, and (iii) the rotation direction 145*a* or 145*b* of the drive shaft 136 during use, as described above in reference to FIGS. 18 and 19, provide particular operational advantages in some usage scenarios. For example, as described above in reference to FIG. 1, when the direction of rotation and the direction the filars are wound are the same direction, the winds of the filars will tend to radially expand (the drive shaft 136 will tend to "open up"), resulting in less friction, no need for lubrication, less stress induced on the guidewire, and so on. Additionally, when the direction of rotation of the drive shaft 136 and the direction of the spiral path defined by the centers of mass of the abrasive elements 144 are opposite, such an arrangement can advantageously provide a smoother running and more controllable atherectomy procedure as compared to systems that rotate the drive shaft in the same direction as the spiral path defined by the centers of mass of the abrasive elements. For example, rather than causing the abrasive elements 144 to corkscrew into the stenotic lesion material (as can occur when the drive shaft rotational direction is the same as the direction of the spiral path defined by the centers of mass of the abrasive elements), the abrasive elements 144 can instead abrade the stenotic lesion material in more of a gradual, smooth, and controllable manner.

A number of embodiments of the invention have been described. Nevertheless, it will be understood that various modifications may be made without departing from the spirit and scope of the invention. For example, design features of the embodiments described herein can be combined with other design features of other embodiments described herein. Accordingly, other embodiments are within the scope of the following claims.

What is claimed is:

1. A rotational atherectomy apparatus for removing stenotic lesion material from a blood vessel of a patient, the apparatus comprising:

an elongate flexible drive shaft defining a longitudinal axis and comprising a torque-transmitting coil of one or more filars that are helically wound around the longitudinal axis in a first spiral direction along an entire length of the elongate flexible drive shaft; and five abrasive elements attached to the one or more filars of the torque-transmitting coil at a distal end portion of the drive shaft and each having a center of mass offset from the longitudinal axis, the five abrasive elements including: (i) a proximal-most abrasive element, (ii) a distal-most abrasive element, and (iii) three middle abrasive elements located between the proximal-most and distal most abrasive elements, wherein the three middle abrasive element have larger outer diameters than the proximal-most and distal-most abrasive elements, a path defined by the centers of mass of the five abrasive elements spiraling around the longitudinal axis in a second spiral direction that is opposite of the first spiral direction.

2. The apparatus of claim 1, wherein the drive shaft is configured to rotate about the longitudinal axis in the first spiral direction such that the abrasive elements orbit around the longitudinal axis.

3. The apparatus of claim 1, wherein, when viewed in a distal direction from a proximal end of the drive shaft, the first spiral direction is clockwise and the second spiral direction is counterclockwise.

4. The apparatus of claim 1, wherein, when viewed in a distal direction from a proximal end of the drive shaft, the first spiral direction is counterclockwise and the second spiral direction is clockwise.

5. The apparatus of claim 1, wherein the rotational atherectomy is performed without using a lubricant between the drive shaft and a guidewire that is disposed within a lumen defined by the drive shaft.

6. The apparatus of claim 1, further comprising a guidewire configured to be navigated within the patient's vasculature to a target location within the blood vessel.

7. The apparatus of claim 6, wherein a distal end portion of the guidewire is deliverable past a lesion comprising the stenotic lesion material.

8. The apparatus of claim 7, wherein the drive shaft is configured to be inserted over the guidewire.

9. The apparatus of claim 8, wherein the drive shaft remains over the guidewire during the rotating, and wherein the distal end portion of the guidewire extends distally of a distal end of the drive shaft during the rotating.

10. The apparatus of claim 8, wherein the drive shaft comprises a distal-most extension portion that extends distally of a distal-most abrasive element of the five abrasive elements, and wherein at least a portion of the distal-most extension portion is deliverable through the lesion when the apparatus is delivered into the blood vessel.

11. The apparatus of claim 10, wherein the drive shaft comprises a metallic concentric stability element having a cylindrical shape and a center of mass aligned with the longitudinal axis, the stability element fixed to the drive shaft, and wherein the metallic concentric stability element is distally spaced apart from a distal-most abrasive element of the five abrasive elements.

12. The apparatus of claim 11, wherein the metallic concentric stability element is deliverable through the lesion when the rotational atherectomy device is delivered into the blood vessel.

13. The apparatus of claim 12, wherein the metallic concentric stability element has an abrasive coating on an exterior of the metallic concentric stability element.

14. The apparatus of claim 8, wherein the drive shaft comprises a concentric tip member affixed to and extending distally from a distal-most end of the drive shaft, wherein the concentric abrasive tip member defines a central opening through which the guidewire extends.

15. The apparatus of claim 14, wherein the drive shaft comprises a distal-most extension portion that extends distally of a distal-most abrasive element of the five abrasive elements, and wherein at least a portion of the distal-most extension portion is deliverable past the lesion when the rotational atherectomy device is delivered into the blood vessel, and wherein the concentric tip member has a maximum outer diameter that is smaller than or equal to an outer diameter of the distal-most extension portion of the drive shaft.

16. A rotational atherectomy apparatus for removing stenotic lesion material from a blood vessel of a patient, the apparatus comprising:

an elongate flexible drive shaft defining a longitudinal axis and comprising a torque-transmitting coil of one or more filars that are helically wound around the longitudinal axis in a first spiral direction along an entire length of the elongate flexible drive shaft; and five abrasive elements attached to the one or more filars of the torque-transmitting coil at a distal end portion of the drive shaft and each having a center of mass offset from the longitudinal axis, the five abrasive elements including: (i) a proximal-most abrasive element, (ii) a distal-most abrasive element, and (iii) three middle abrasive elements located between the proximal-most and distal most abrasive elements, wherein all of the five abrasive elements have equal outer diameters, a path defined by the centers of mass of the five abrasive elements spiraling around the longitudinal axis in a second spiral direction that is opposite of the first spiral direction.

17. The apparatus of claim 16, wherein, when viewed in a distal direction from a proximal end of the drive shaft, the first spiral direction is clockwise and the second spiral direction is counterclockwise.

18. The apparatus of claim 16, wherein, when viewed in a distal direction from a proximal end of the drive shaft, the first spiral direction is counterclockwise and the second spiral direction is clockwise.

19. The apparatus of claim 16, wherein further comprising a guidewire configured to be navigated to a target location within the blood vessel, the drive shaft being deliverable over the guidewire.

20. The apparatus of claim 16, wherein the drive shaft comprises a distal-most extension portion that extends distally of a distal-most abrasive element of the five abrasive elements, and wherein at least a portion of the distal-most extension portion is deliverable through the lesion when the apparatus is delivered into the blood vessel.

21. The apparatus of claim 20, wherein the drive shaft comprises a metallic concentric stability element having a cylindrical shape and a center of mass aligned with the longitudinal axis, the stability element fixed to the drive shaft, and wherein the metallic concentric stability element is distally spaced apart from a distal-most abrasive element of the five abrasive elements.

22. A rotational atherectomy apparatus for removing stenotic lesion material from a blood vessel of a patient, the apparatus comprising:

an elongate flexible drive shaft defining a longitudinal axis and comprising a torque-transmitting coil of one or more filars that are helically wound around the longitudinal axis in a first spiral direction along an entire length of the elongate flexible drive shaft; and at least four abrasive elements attached to the one or more filars of the torque-transmitting coil at a distal end portion of the drive shaft and each having a center of mass offset from the longitudinal axis, a spiral path defined by the centers of mass of the at least four abrasive elements spiraling around the longitudinal axis in a second spiral direction that is opposite of the first spiral direction, an overall radial angle of the spiral path is defined by a radial angle between a distal-most abrasive element of the at least four abrasive elements and a proximal-most abrasive element of the at least four abrasive elements, wherein the overall radial angle of the spiral path is always less than 180 degrees along any 10 cm length of the distal end portion of the drive shaft.

23. The apparatus of claim 22, wherein, when viewed in a distal direction from a proximal end of the drive shaft, the first spiral direction is clockwise and the second spiral direction is counterclockwise.

24. The apparatus of claim 22, wherein, when viewed in a distal direction from a proximal end of the drive shaft, the first spiral direction is counterclockwise and the second spiral direction is clockwise.

25. The apparatus of claim 22, wherein further comprising a guidewire configured to be navigated to a target location within the blood vessel, the drive shaft being deliverable over the guidewire.

26. The apparatus of claim 22, wherein the drive shaft comprises a distal-most extension portion that extends distally of a distal-most abrasive element of the at least four abrasive elements, and wherein at least a portion of the distal-most extension portion is deliverable through the lesion when the apparatus is delivered into the blood vessel.

27. The apparatus of claim 26, wherein the drive shaft comprises a metallic concentric stability element having a cylindrical shape and a center of mass aligned with the longitudinal axis, the stability element fixed to the drive shaft, and wherein the metallic concentric stability element is distally spaced apart from a distal-most abrasive element of the at least four abrasive elements.

28. A rotational atherectomy apparatus for removing stenotic lesion material from a blood vessel of a patient, the apparatus comprising:
a guidewire;
an elongate flexible drive shaft defining a longitudinal axis and comprising a torque-transmitting coil of one or more filars that are helically wound around the longitudinal axis in a first spiral direction, wherein the one or more filars are exposed to an interior lumen of the drive shaft; and
a series of abrasive elements attached to a distal end portion of the drive shaft that includes at least three equally sized abrasive elements, each abrasive element in the series of abrasive elements having a center of mass offset from the longitudinal axis, a spiral path defined by the centers of mass of the series of abrasive elements including said at least three equally sized abrasive elements spiraling around the longitudinal axis in a second spiral direction that is opposite of the first spiral direction, an overall radial angle of the spiral path is defined by a radial angle between a distal-most abrasive element of the series of abrasive elements and a proximal-most abrasive element of the series of abrasive elements, wherein the overall radial angle of the spiral path is always less than 180 degrees along any 10 cm length of the distal end portion of the drive shaft,
wherein the guidewire is positionable within a lumen defined by the drive shaft during rotation of the drive shaft without using a lubricant between the drive shaft and the guidewire.

29. The apparatus of claim 28, wherein the drive shaft is configured to rotate about the longitudinal axis in the first spiral direction such that the abrasive elements orbit around the longitudinal axis.

30. The apparatus of claim 28, wherein the series of abrasive elements includes five abrasive elements, the five abrasive elements including: (i) a proximal-most abrasive element, (ii) a distal-most abrasive element, and (iii) said three equally sized abrasive elements located between the proximal-most and distal most abrasive elements.

* * * * *